United States Patent
Hacker et al.

(10) Patent No.: US 6,750,177 B2
(45) Date of Patent: Jun. 15, 2004

(54) HERBICIDE COMBINATION WITH ACYLATED AMINOPHENYLSULFONYLUREAS

(75) Inventors: Erwin Hacker, Hochheim (DE); Hermann Bieringer, Eppstein (DE); Hansjörg Krähmer, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 10/382,004

(22) Filed: Mar. 5, 2003

(65) Prior Publication Data

US 2003/0176284 A1 Sep. 18, 2003

(30) Foreign Application Priority Data

Mar. 5, 2002 (DE) .......................... 102 09 430

(51) Int. Cl.[7] .................. A01N 47/36; A01N 43/54; A01N 43/66
(52) U.S. Cl. .................. 504/128; 504/132; 504/134; 504/135
(58) Field of Search .................. 504/134, 135, 504/128, 132

(56) References Cited

U.S. PATENT DOCUMENTS

| | | | |
|---|---|---|---|
| 4,601,747 A | 7/1986 | Willms et al. | |
| 5,463,081 A | 10/1995 | Ort et al. | |
| 5,648,315 A | 7/1997 | Lorenz et al. | |
| 5,688,745 A | 11/1997 | Ort et al. | |
| 5,922,646 A | 7/1999 | Schnabel et al. | |
| 5,925,597 A | 7/1999 | Lorenz et al. | |
| 6,239,306 B1 | 5/2001 | Lorenz et al. | |
| 6,498,253 B1 | 12/2002 | Schnabel et al. | |

FOREIGN PATENT DOCUMENTS

| | | |
|---|---|---|
| CA | 2390570 | 5/2001 |
| DE | 198 34 629 A1 | 12/1998 |
| DE | 198 42 894 A1 | 3/2000 |
| EP | 0 131 258 A2 | 1/1985 |
| WO | WO-92/13845 | 8/1992 |
| WO | WO-95/10507 A2 | 4/1995 |
| WO | WO-95/29899 | 11/1995 |
| WO | WO-01/35741 A2 | 5/2001 |
| WO | WO-02/01957 A1 | 1/2002 |

OTHER PUBLICATIONS

EPA Pesticide Program Update. EPA Office of Pesticide Programs. Apr. 27, 2000. http://www.epa.gov/pesticides.*
Baron, J. "IR-4 New Products/Transitional Solution List—Nov. 2000". p. 1 and 4.*
Bollettino fitosanitario [Phytosanitary Bulletin]. Servizio fitosanitario cantonale. Feb. 4, 2002.*
Wiesbrook, Michelle. "Agronomic" Illinois Pesticide Review. vol. 2002, Issue 4. Jul. 2002.*

(List continued on next page.)

Primary Examiner—S. Mark Clardy
(74) Attorney, Agent, or Firm—Connolly Bove Lodge & Hutz LLP

(57) ABSTRACT

Herbicidal compositions with acylated aminophenylsulfonylureas

Herbicide combinations with an effective content of components (A), (B) and (C) have improved herbicidal effects:
(A) one or more herbicides selected from the group of the compounds of the formula (I) or their salts,

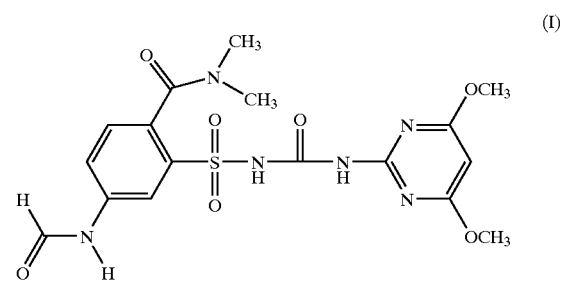

(B) denotes one or more herbicides from the group of the compounds of the formula (II) and their salts,

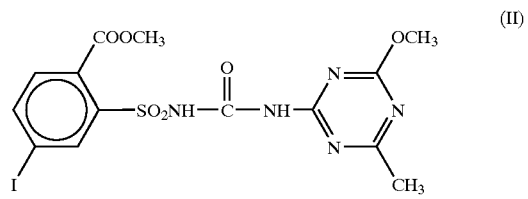

(C) denotes one or more herbicides from the group of the compounds consisting of (C1) flumioxazin (C2) alachlor (C3) metolachlor (C4) acetochlor (C5) dimethenamid (C6) pethoxamid (C7) atrazine (C8) simazone (C9) cyanazine (C10) terbuthylazine (C11) metribuzin (C12) isoxaflutole (C13) fluthiamid (C14) terbutryne (C15) nicosulfuron (C16) rimsulfuron (C17) primsulfuron (C18) pendimethalin (C19) sulcotrione (C20) dicamba (C21) mesotrione (C22) linuron (C23) benoxacor (C24) metosulam (C25) flumetsulam (C26) sethoxydim (C27) cycloxydim (C28) clethodim (C29) clefoxidim (C30) aclonifen (C31) MCPA (C32) 2, 4-D (C33) bromoxynil (C34) bentazone (C35) fluthiacet (C36) pyridate (C37) diflufenzopyr (C38) carfentrazone (C39) clopyralid (C40) halosulfuron (C41) thifensulfuron (C42) prosulfuron (C43) tritosulfuron (C44) sulfosulfuron (C45) ethoxysulfuron (C46) tribenuron (C47) amidosulfuron (C48) mecoprop (C49) dichlorporp (C50) fluroxypyr (C51) profluazol (C52) amicarbazone (C53) trifloxysulfuron (C54) glufosinate (C55) glufosinate-ammonium (C56) glyphosate (C57) glyphosate-isopropytammonium (C58) imazapyr (C59) imazethapyr (C60) imazamethabenz (C61) imazamox (C62) imazaquin and (C63) imazapic (AC 263,222).

10 Claims, No Drawings

OTHER PUBLICATIONS

NDSU. North Dakota Pesticide Quarterly. "Coordinator's Comments". 21(1). Jan. 2003.*

Thomson Derwent English language abstract of DE 198 34 629 A1 (1998).

Thomson Derwent English language abstract of DE 198 42 894 A1 (2000).

Adamczewski Kazimierz et al; "Evaluation of Iodosulfuron and Amidosulfuron Mixture to Control Broad–Leaved Weeds in Winter and Spring Cereals;" Journal of Plant Protection Research; Bd. 41, Nr. 2, 2001, pp. 101–108 (2001).

Thomson Derwent English language abstract of WO 02/01957 A1 (2002).

Thomson Derwent English language abstract of WO 01/35741 A2 (2001).

U.S. application Ser. No. 10/382,031, filed Mar. 5, 2003; Herbicide Combinations Comprising Specific Sulfonylureas; Hacker, et al.

U.S. application Ser. No. 10/379,634, filed Mar. 5, 2003; Herbicidal Combinations Comprising Specific Sulfonylureas; Hacker, et al.

S. Pelte, et al.: "Le Mesosulfuron–methyl, Herbicide bles tendres, bles durs, seigle et triticale;" Phytoma, Nr. 550, Jun. 2002, pp. 52–54.

\* cited by examiner

HERBICIDE COMBINATION WITH ACYLATED AMINOPHENYLSULFONYLUREAS

DESCRIPTION

Herbicide combination with acylated aminophenylsulfonylureas

The invention is in the technical field of crop protection products which can be employed against harmful plants, for example in plant crops, and which comprise, as active ingredients, a combination of at least three herbicides.

The publications WO 95/29899 and WO 92/13845 disclose sulfonylureas and their salts and also their use as herbicides and/or plant growth regulators.

The efficacy of these herbicides against harmful plants in the plant crops is at a high level, but depends in general on the application rate, the formulation in question, the harmful plants or spectrum of harmful plants to be controlled in each case, the climatic conditions, the soil conditions and the like. Another criterion is the duration of action, or the breakdown rate of the herbicide. If appropriate, changes in the sensitivity of harmful plants, which may occur upon prolonged use of the herbicides or within geographic limitations must also be taken into consideration. The compensation of losses in action in the case of individual harmful plants by increasing the application rates of the herbicides is only possible to a certain degree, for example because such a procedure frequently reduces the selectivity of the herbicides or because the action is not improved, even when applying higher rates. In some cases, the selectivity in crops can be improved by adding safeners. In general, however, there remains a need for methods to achieve the herbicidal action with a lower application rate of active ingredients. Not only does a lower application rate reduce the amount of an active ingredient required for application, but, as a rule, it also reduces the amount of formulation auxiliaries required. It both reduces the economic input and improves the ecological compatibility of the herbicide treatment.

One possibility of improving the application profile of a herbicide can consist in combining the active ingredient with one or more other active ingredients. However, the combined use of a plurality of active ingredients does not infrequently cause phenomena of physical and biological incompatibility, for example a lack of stability in a coformulation, decomposition of an active ingredient, or antagonism of the active ingredients. Desired, in contrast, are combinations of active-ingredients with an advantageous activity profile, high stability and if possible a synergistically improved action, which allows reduction of the application rate in comparison with the individual application of the active ingredients to be combined.

Surprisingly, it has now been found that certain active ingredients from the group of the acylated aminophenylsulfonylureas in combination with certain structurally different herbicides act together in a particularly advantageous manner, for example when they are employed in plant crops which are suitable for the selective use of the herbicides, if appropriate with addition of safeners.

The invention therefore relates to herbicide combinations with an effective content of components (A), (B) and (C), where (A) denotes one or more herbicides from the group of the compounds of the formula (I) or their salts,

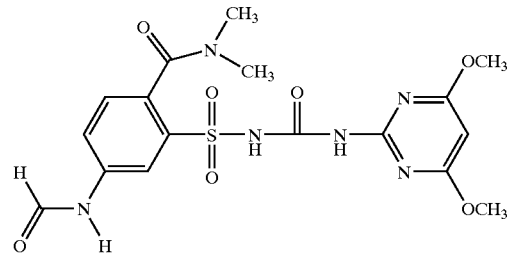

(B) denotes one or more herbicides from the group of the compounds of the formula (II) or their salts,

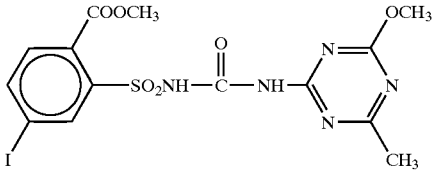

and (C) denotes one or more herbicides from the group of the compounds consisting of (referred to by the "common names" under the reference "The Pesticide Manual" 11th Ed., British Crop Protection Council 1997, abbreviated to "PM")

(CI) herbicides which are selective in cereals and/or some dicotyledonous crops and act against monocotyledonous and -dicotyledonous harmful plants, which herbicides are selected from the group consisting of:

(C1) flumioxazin (PM, pp. 576-577), for example N-(7-fluoro-3,4-dihydro-3-oxo-4-prop-2-inyl-2H-1,4-benzoxazin-6-yl)cyclohex-1-ene-1,2-dicarboxamide, (application rate: 10-500 g AS/ha, preferably 20-400 g AS/ha; application ratio (A+B)/C=1:25-50:1, preferably 1:10-20:1);

(C2) alachlor (PM, pp. 23-24), for example 2-chloro-N-(2,6-diethylphenyl)-N-(methoxymethyl)acetamide, (application rate: 100-5000 g AS/ha, preferably 300-4000 g AS/ha; application ratio (A+B)/C=1:500-3:1, preferably 1:250-1:1);

(C3) metolachlor (PM, pp.833-834), for example 2-chloro-N-(2-ethyl-6-methylphenyl)-N-(2-methoxy-1-methylethyl)acetamide, (application rate: 100-5000 g AS/ha, preferably 300-4000 g AS/ha; application ratio (A+B)/C=1:500-3:1, preferably 1:250-1:1);

(C4) acetochlor (PM, pp. 10-12), for example 2-chloro-N-(ethoxymethyl)-N-(2-ethyl-6-methylphenyl)-acetamide, (application rate: 100-5000 g AS/ha, preferably 300-4000 g AS/ha; application ratio (A+B)/C=1:500-3:1, preferably 1:250-1:1);

(C5) dimethenamid (PM, pp. 409-410), for example 2-chloro-N-(2,4-dimethyl-3-thienyl)-N-(2-methoxy-1-methylethyl)acetamide, (application rate: 100-5000 g AS/ha, preferably 300-4000 g AS/ha; application ratio (A+B)/C=1:500-3:1, preferably 1:250-1:1);

(C6) pethoxamide (AG Chem, New Compound Review (publ. Agranova), Vol.17, 1999, p. 94, for example 2-chloro-N-(2-ethoxyethyl)-N-(2-methyl-1-phenyl-1-propenyl)acetamide, (application rate: 100-5000 g AS/ha, preferably 300-4000 g AS/ha; application ratio (A+B)/C=1:500-3:1, preferably 1:250-1:1);

(C7) atrazine (PM, pp. 55-57), for example N-ethyl-N-isopropyl-6-chloro-2,4-diamino-1,3,5-triazine, (application rate: 100-5000 g AS/ha, preferably 300-4000 g AS/ha; application ratio (A+B)/C=1:500-3:1, preferably 1:250-1:1);

(C8) simazine (PM, pp. 1106-1108), for example 6-chloro-N,N-diethyl-2,4-diamino-1,3,5-triazine (application rate: 100-5000 g AS/ha, preferably 300-4000 g AS/ha; application ratio (A+B)/C=1:500-3:1, preferably 1:250-1:1);

(C9) cyanazine (PM, pp. 280-283), for example 2-(4-chloro-6-ethylamino-1,3,5-triazin-2-ylamino)-2-methylpropionitrile, (application rate: 100-500 9 AS/ha, preferably 300-4000 g AS/ha; application ratio (A+B)/C=1:500-3:1, preferably 1:250-1:1);

(C10) terbuthylazine (PM, pp.1168-1170), for example N-ethyl-N-tert-butyl-6-chloro-2,4-diamino-1,3,5-triazine, (application rate: 100-5000 g AS/ha, preferably 300-4000 g AS/ha; application ratio (A+B)/C=1:500-3:1, preferably 1:250-1:1);

(C11) metribuzin (PM, pp. 840-841), for example 4-amino-6-tert-butyl-3-methylthio-1,2,4-triazin-5(4H)-one, (application rate: 10-3000 g AS/ha, preferably 20-2000 g AS/ha; application ratio (A+B)/C=1:300-25:1, preferably 1:100-10:1);

(C12) isoxaflutole (PM, pp. 737-739), for example (5-cyclopropyl-4-isoxazolyl)[2-(methylsulfonyl)-4-(trifluoromethyl)phenyl]methanone, (application rate: 10-3000 g AS/ha, preferably 20-2000 g AS/ha; application ratio (A+B)/C=1:300-25:1, preferably 1:100-10:1);

(C13) fluthiamid (=flufenacet=BAY FOE 5043) (PM, pp. 82-83), for example 4'-fluoro-N-isopropyl-2-(5-trifluoromethyl-1,3,4-thiadiazol-2-yloxy)acetanilide, (application rate: 10-3000 g AS/ha, preferably 20-2000 g AS/ha; application ratio (A+B)/C=1:300-25:1, preferably 1:100-10:1);

(C14) terbutryne (PM, pp.1170-1172), for example N-(1,1-dimethylethyl)-N-ethyl-6-(methylthio)-1,3,5-triazine-2,4-diamine, (application rate: 10-3000 g AS/ha, preferably 20-2000 g AS/ha; application ratio (A+B)/C=1:500-3:1, preferably 1:250-1:1);

(C15) nicosulfuron (PM, pp. 877-879), for example 2-(4,6-dimethoxypyrimidin-2-yl)-3-(3-dimethylcarbamoyl-2-pyridylsulfonyl)urea and its salts, (application rate: 1-120 g AS/ha, preferably 2-909 AS/ha; application ratio (A+B)C=1:12-240:1, preferably 1:5-100:1);

(C16) rimsulfuron (PM, pp. 1095-1097), for example 1-(4,6-dimethoxypyrimidin-2-yl)-3-(3-ethylsulfonyl-2-pyridylsulfonyl)urea and its salts, (application rate: 1-120 g AS/ha, preferably 2-90 g AS/ha; application ratio (A+B)/C=1:12-240:1, preferably 1:5-100:1);

(C17) primisulfuron, also comprising its esters, such as the methyl ester (PM, pp. 997-999), for example 2-[4,6-bis(difluoromethoxy)pyrimidin-2-ylcarbamoylsulfamoyl]benzoic acid or its methyl ester, and its salts, (application rate: 1-120 g AS/ha, preferably 2-90 g AS/ha; application ratio (A+B)/C=1:12-240:1, preferably 1:5-100:1);

(C18) pendimethalin (PM, pp. 937-939), for example N-(1-ethylpropyl)-2,6-dinitro-3,4-xylidine, (application rate: 100-5000 g AS/ha, preferably 200-4000 g AS/ha; application ratio (A+B)/C=1:500-3:1, preferably 1:200-1:1);

(C19) sulcotrione (PM, pp. 1124-1125), for example 2-(2-chloro-4-mesylbenzoyl)cyclohexane-1,3-dione, (application rate: 5-1500 g AS/ha, preferably 10-1000 g AS/ha; application ratio (A+B)/C=1:150-50:1, preferably 1:50-20:1);

(C20) dicamba (PM, pp. 356-357), for example 3,6-dichloro-o-anisic acid and its salts, (application rate: 5-1500 g AS/ha, preferably 10-1000 g AS/ha; application ratio (A+B)/C=1:150-50:1, preferably 1:50-20:1);

(C21) mesotrione, for example 2-(4-mesyl-2-nitrobenzoyl)cyclohexane-1,3-dione (ZA 1296, cf. Weed Science Society of America (WSSA) in WSSA Abstracts 1999, Vol. 39, pages 65-66, numbers 130-132), (application rate: 5-1500 g AS/ha, preferably 10-1000 g AS/ha; application ratio (A+B)/C=1:150-50:1, preferably 1:50-20:1);

(C22) linuron (PM, pp. 751-753), for example 3-(3,4-dichlorophenyl)-1-methoxy-1-methylurea, (application rate: 100-5000 g AS/ha, preferably 200-4000 g AS/ha; application ratio (A+B)/C=1:500-3:1, preferably 1:200-1:1);

(C23) benoxacor (PM, pp.102-103), for example (±)-4-dichloroacetyl-3,4-dihydro-3-methyl-2H-1,4-benzoxazine, (application rate: 5-1500 g AS/ha, preferably 10-1000 g AS/ha; application ratio (A+B)/C=1:150-50:1, preferably 1:50-20:1);

(C24) metosulam (PM, pp. 836-838), for example 2',6'-dichloro-5,7-dimethoxy-3'-methyl[1,2,4]triazolo[1,5-a]pyrimidine-2-sulfonamide, (application rate: 5-1500 g AS/ha, preferably 10-1000 g AS/ha; application ratio (A+B)/C=1:150-50:1, preferably 1:50-20:1);

(C25) flumetsulam (PM, pp. 573-574), for example 2',6'-difluoro-5-methyl[1,2,4]triazolo[1,5-a]pyrimidine-2-sulfonamide, (application rate: 5-1500 g AS/ha, preferably 10-1000 g AS/ha; application ratio (A+B)/C=1:150-50:1, preferably 1:50-20:1);

(C26) sethoxydim (PM, pp.1101-1103), for example (±)-(EZ)-(1-ethoxyiminobutyl)-5-[2-ethylthio)propyl]-3-hydroxycyclohex-2-enone, (application rate: 10-5000 g AS/ha, preferably 20-3000 g AS/ha; application ratio (A+B)/C=1:500-25:1, preferably 1:150-1:1);

(C27) cycloxydim (PM, pp.290-291), for example (±)-2-[1-ethoxyimino)butyl]-3-hydroxy-5-thian-3-ylcyclohex-2-enone, (application rate: 10-5000 g AS/ha, preferably 20-3000 g AS/ha; application ratio (A+B)/C=1:500-25:1, preferably 1:150-1:1);

(C28) clethodim (PM, pp. 250-251), for example (±)-2-[(E)-1-[(E)-3-chloroallyloxyimino]propyl]-5-[2-(ethylthio)propyl]-3-hydrocyclohex-2-enone, (application rate: 10-5000 g AS/ha, preferably 20-3000 g AS/ha; application ratio (A+B)/C=1:500-25:1, preferably 1:150-1:1);

(C29) clefoxidim, for example 2-[1-(2-(4-chlorophenoxy)-propoxyimino)butyl]-3-oxo-5-thion-3-ylcyclohex-1-enol (AG Chem, New Compound Review (publ. Agranova), Vol.17,1999, p. 26), (application rate: 10-5000 g AS/ha, preferably 20-3000 g AS/ha; application ratio (A+B)/C=1:500-25:1, preferably 1:150-1:1);

(CII) herbicides which act selectively in some dicotyledonous crops predominantly, against dicotyledonous harmful plants, selected from the group consisting of (C30) aclonifen, in particular also including its salts, such as the sodium salt, (PM, pp. 14-15), for example 2-chloro-6-nitro-3-phenoxyanilin, (application rate in general: 50-5000 g AS/ha, preferably 200-3000 g AS/ha; application ratio (A+B)/C=1:5000-2:1, preferably 1:600-1:3);

(C31) MCPA (PM, pp. 770-771), for example (4-chloro-2-methylphenoxy)acetic acid, predominantly employed forms, inter alia, MCPA-butotyl, MCPA-dimethylammonium, MCPA-isoctyl, MCPA-potassium.

MCPA-sodium, (application rate: 50-5000 g AS/ha, preferably 100-3000 g AS/ha; application ratio (A+B)/C=1:500-5:1, preferably 1:150-2:1);

(C32) 2,4-D (PM, pp. 323-327), for example (2,4-dichloro-phenoxy)acetic acid, frequently employed forms: 2,4-D-butotyl, 2,4-D-butyl, 2,4-D-dimethylammonium, 2,4-D-diolamine, 2,4-D-isooctyl, 2,4-D-isopropyl, 2,4-D-trolamine, (application rate in general: 50-5000 g AS/ha, preferably 100-3000 g AS/ha; application ratio (A+B)/C= 1:500-5:1, preferably 1:150-2:1);

(C33) bromoxynil (PM, pp. 149-151), for example 3,5-dibromo-4-hydroxybenzonitrile, (application rate: 25-1000 g AS/ha, preferably 50-500 g AS/ha; application ratio (A+B)/C=1:100-10:1, preferably 1:25-4:1)

(C34) bentazone (PM, pp. 1064-1066), for example 3-isopropyl-2,2-dioxo-1H-2,1,3-benzothiadiazine-4(3H)-one, (application rate: 25-1000 g AS/ha, preferably 50-500 g AS/ha; application ratio (A+B)/C=1:100-10:1, preferably 1:25-4:1);

(C35) fluthiacet (PM, pp. 606-608), for example [2-chloro-4-fluoro-5-[5,6,7,8-tetrahydro-3-oxo-1 H,3H-1,3,4-thiadiazolo[3,4-a]pyridazine-1-ylideneamino)phenylthio] acetic acid and preferably the methyl ester, (application rate: 100-5000 g AS/ha, preferably 200-3000 g AS/ha; application ratio (A+B)/C=1:500-3:1, preferably 1:150-1:1);

(C36) pyridate (PM, pp.1064-1066), for example O-6-chloro-3-phenylpyridazin-4-yl) S-octyl thiocarbonate, (application rate:
100-5000 g AS/ha, preferably 200-3000 g AS/ha; application ratio (A+B)/C=1:500-3:1, preferably 1:150-1:1);

(C37) diflufenzopyr (BAS 65 00 H, PM, pp. 81-82), for example 2-{1-[4-(3,5-difluorophenyl)semicarbazono] ethyl}nicotinic acid, (application rate in general: 1-500 g AS/ha, preferably 2-300 g AS/ha; application ratio (A+B)/C=1:50-250:1, preferably 1:15-1:1);

(C38) carfentrazone (PM, pp. 191-193), for example ethyl (RS)-2-chloro-3-[2-chloro-5-(4-difluoromethyl-4,5-dihydro-3-methyl-5-oxo-1 H-1,2,4-triazol-1-yl)-4-fluorophenyl]propionate, also applied as, inter alia, carfentrazone-ethyl (as stated) or else as the acid, (application rate: 1-500 g AS/ha, preferably 2-300 g AS/ha; application ratio (A+B)/C=1:50-250:1, preferably 1:15-1:1);

(C39) clopyralid (PM, pp. 260-263), for example 3,6-dichloropyridin-2-carboxylic acid, (application rate: 1-300 g AS/ha, preferably 2-200 g AS/ha; application ratio (A+B)/C=1:30-250:1, preferably 1:10-100:1);

(C40) halosulfuron, (PM, pp. 657-659), for example 3-chloro-5-(4,6-dimethoxypyrimidin-2-ylcarbamoylsulfamoyl)-1-methylpyrazole-4-carboxylic acid and its esters and salts, preferably the methyl ester, (application rate in general: 1-300 g AS/ha, preferably 2-200 g AS/ha; application ratio (A+B)/C=1:30-250:1, preferably 1:10-100:1);

(C41) thifensulfuron, also including its esters and salts, preferably the methyl ester (PM, pp.1188-1190), for example 3-[[[[(4-methoxy-6-methyl-1,3,5-triazin-2-yl)amino]carbonyl]amino]sulfonyl]-2-thiophenecarboxylic acid or its methyl ester and its salts, (application rate: 1-300 g AS/ha, preferably 2-200 g AS/ha; application ratio (A+B)/C=1:30-250:1, preferably 1:10-100:1);

(C42) prosulfuron, also including its esters and salts, (PM, pp.1041-1043), for example 1-(4-methoxy-6-methyl-1,3,5-triazin-2-yl)-3-[2-(3,3,3-trifluoropropyl)phenylsulfonyl] urea and its salts, (application rate: 1-300 g AS/ha, preferably 2-200 g AS/ha; application ratio (A+B)/C=1:30-250:1, preferably 1: 10-100:1);

(C43) tritosulfuron, also including its esters and salts, (AG Chem, New Compound Review (publ. Agranova), Vol. 17, 1999, p. 24), for example N-[[[4'-methoxy-6-(trifluoromethyl)-1,3,5-triazi n-2-yl]amino]carbonyl]-2-trifluoromethylbenzenesulfonamide], (application rate: 0.1-200 g AS/ha, preferably 0.5-100 g AS/ha; application ratio (A+B)/C=1:20-2500:1, preferably 1:5-400:1);

(C44) sulfosulfuron, also including its esters and salts, (PM, pp.1130-1131), for example 1-(4,6-dimethoxypyridin-2-yl)-3-(2-ethylsulfonylimidazol[1,2-a]pyridin-3-yl) sulfonylurea, (application rate: 0.1-200 g AS/ha, preferably 0.5-100 g AS/ha; application ratio (A+B)/C=1:20-2500:1, preferably 1:5-400:1);

(C45) ethoxysulfuron, also including its esters and salts, (PM, pp. 488-490), for example 1-(4,6-dimethoxypyrimidin-2-yl)-3-(2-ethoxyphenoxysulfonyl) urea, (application rate: 5-150 g AS/ha, preferably 10-100 g AS/ha; application ratio (A+B)/C=1:15-50:1, preferably 1:5-10:1);

(C46) tribenuron, also including its esters and salts, (PM, pp. 1230-1232), for example methyl 2-[[[[4-methoxy-6-methyl-1,3,5-triazin-2-yl)methylamino]carbonyl]amino] sulfonyl]benzoate, (application rate: 1-100 g AS/ha, preferably 2-80 g AS/ha; application ratio (A+B)/C=1:10-250:1, preferably 1:5-100:1);

(C47) amidosulfuron, also including its esters and salts, (PM, pp. 37-38), for example 1-(4,6-dimethoxypyridin-2-yl)-3-mesyl(methyl)sulfamoylurea (application rate: 1-100 g AS/ha, preferably 2-80 g AS/ha; application ratio (A+B)/C=1:10-250:1, preferably 1:5-100:1);

(C48) mecoprop, also including mecoprop-p and the esters and salts, (PM, pp. 776-779), for example (RS)-2-(4-chloro-o-tolyloxy)propionic acid, (application rate: 50-5000 g AS/ha, preferably 100-3000 g AS/ha; application ratio (A+B)/C=1:500-5:1, preferably 1:150-2:1);

(C49) dichlorprop, also including dichlorprop-p and the esters and salts, (PM, pp. 368-372), for example (RS)-2,4-dichlorophenoxy) propionic acid, (application rate: 50-5000 g AS/ha, preferably 100-3000 g AS/ha; application ratio (A+B)/C=1:500-5:1, preferably 1:150-2:1);

(C50) fluroxypyr, (PM, pp. 597-600), for example 4-amino-3,5-dichloro-6-fluoro-2-pyridyloxyacetic acid, (application rate: 5-500 g AS/ha, preferably 10-300 g AS/ha; application ratio (A+B) /C=1:50-50:1, preferably 1:15-20:1);

(CIII) herbicides which act selectively in some mono-/dicotyledonous crops, predominantly against monocotyledonous harmful plants, selected from the group consisting of (C51) profluazole (AGROW, No. 338 Oct. 15, 1999, p. 26, PJB Publications Ltd. 1999, WO 97/15576), for example 1 -chloro-N-[2-chloro-4-fluoro-5-[(6S, 7aR)-6-fluorotetrahydro-1,3-dioxo-1 H-pyrrolo[1,2-c]imidazol-2 (3H)-yl]phenyl]methanesulfonamide, (application rate 5-1000 g AS/ha, preferably 5-800 g AS/ha; quantitative ratio (A+B)/C=1:350-25:1, preferably 1:160-10:1);

(C52) amicarbazone (AGROW, No. 338 October 15, 1999, p. 26, PJB Publications Ltd. 1999, DE 3839206), for example 4-amino-N-(1,1 -dimethylethyl)-4,5-dihydro-3-(1-methylethyl)-5-oxo-1 H-1,2,4-triazole-1-carboxamide), (application rate 5-1000 g AS/ha, preferably 5-800 g AS/ha; quantitative ratio (A+B)/C=1:350-50:1, preferably 1:160-40:1);

(C53) trifloxysulfuron, also including its esters and salts, for example the sodium salt, (AGROW, No. 338 October 15, 1999, p. 26, PJB Publications Ltd. 1999, WO 92/16522), for example N-[[(4,6-dimethoxy-2-pyrimidinyl)amino] carbonyl]-3-(2,2,2-trifluoroethoxy)-2-pyridinesulfonamide, (application rate 5-1000 g AS/ha, preferably 5-800 g AS/ha; quantitative ratio (A+B)/C=1:350-25:1, preferably 1:160-10:1);

(CIV) herbicides which are active against monocotyledonous and dicotyledonous harmful plants for use in the nonselective field or in specifically tolerant crops, selected from the group consisting of (C54) glufosinate, (PM, pp. 643-645), for example D,L-2-amino-4-[hydroxy(methyl)phosphinyl]butanoic acid and its salts and esters (application rate: 10-5000 g AS/ha, preferably 25-4000 g AS/ha; application ratio (A+B)/C= 1:500-3:1, preferably 1:200-1:1);

(C55) glufosinate-ammonium, (PM, pp. 643-645), for example amonium 4-[hydroxy(methyl)prosphinoyl]-DL-homoalaninate, the monoammonium salt of the acid form, (application rate: 100-5000 g AS/ha, preferably 250-4000 g AS/ha; application ratio (A+B)/C=1:500-3:1, preferably 1:200-1:1);

(C56) glyphosate, (PM, pp. 646-649), N-(phosphonomethyl)glycine and its salts and esters, (application rate: 100-5000 g AS/ha, preferably 250-4000 g AS/ha; application ratio (A+B)/C=1:500-3:1, preferably 1:200-1:1);

for example (C57) glyphosate-isopropylammonium, (PM, pp. 646-649), for example N-(phosphonomethyl)glycine, (application rate: 100-5000 g AS/ha, preferably 250-4000 g AS/ha; application ratio (A+B)/C=1:500-3:1, preferably 1:200-1:1);

(C58) imazapyr, also including its salts and esters, (PM, pp. 697-699), for example 2-(4-isopropyl-4-methyl-5-oxo-2-imidazol in-2-yl)nicotinic acid, (application rate: 1-1000 g AS/ha, preferably 5-500 g AS/ha; application ratio (A+B)/C=1:100-250:1, preferably 1:25-40:1);

(C59) imazethapyr, also including its salts and esters, (PM, pp. 701-703), (RS)-5-ethyl-2-(4-isopropyl-4-methyl-5-oxo-2-imidazolin-2-yl)nicotinic acid, (application rate: 1-1000 g AS/ha, preferably 5-500 g AS/ha; application ratio (A+B)/C=1:100-250:1, preferably 1:25-40:1);

(C60) imazamethabenz, also including its salts and esters, (PM, pp. 694-696), for example imazamethabenz-methyl, for example methyl (±)-6-(4-isopropyl-4-methyl-5-oxo-2-imid azolin-2-yl)-m-toluate, (application rate: 1-1000 g AS/ha, preferably 5-500 g AS/ha; application ratio -(A+B)/C=1:100-250:1, preferably 1:25-40:1);

(C61) imazamox, also including its salts and esters, (PM, pp. 696-697), for example (RS)-2-(4-isopropyl-4-methyl-5-oxo-2-imidazolin-2-yl)-5-methoxymethylnicotinic acid, (application rate: 1-1000 g AS/ha, preferably 5-500 g AS/ha; application ratio (A+B)/C=1:100-250:1, preferably 1:25-40:1);

(C62) imazaquin, also including its salts and esters, for example the ammonium salt (PM, pp. 699-701), for example (RS)-2-(4-isopropyl-4-methyl-5-oxo-2-imidazolin-2-yl)qu inol in-3-carboxylic acid, (application rate: 1-1000 g AS/ha, preferably 5-500 g AS/ha; application ratio (A+B)/C=1:100-250:1, preferably 1:25-40:1) and (C63) imazapic (AC 263,222), also including its salts and esters, for example the ammonium salt, (PM, pp. 5 and 6, referred to as AC 263,222), for example (RS)-2-(4,5-dihydro-4-isopropyl-4-methyl-5-oxoimidazol-2-yl)-5-methylnicotinic acid, (application rate: 1-1000 g AS/ha, preferably 5-500 g AS/ha; application ratio (A+B)/C=1:100-250:1, preferably 1:25-40:1).

If the abbreviation of the "common name" is used within the present description, it comprises all conventional derivatives, such as the esters and salts, and isomers, in particular the optical isomers, in particular the commercially available form or forms. If the "common name" refers to an ester or salt, this also includes all of the other usual derivatives, such as other esters and salts, the free acids, neutral compounds and isomers, in particular optical isomers, in particular the commercially available form or forms. The chemical compound names stated refer at least to one of the compounds encompassed by the "common name", frequently to a preferred compound. In the case of sulfonamides, such as sulfonylureas, salts also include those which are formed by exchanging a hydrogen atom on the sulfonamide group by a cation.

The herbicide combinations according to the invention have a herbicidally active content of components (A), (B) and (C) and may comprise further components, for example other types of agrochemicals and/or formulation auxiliaries and/or additives conventionally used in crop protection, or they may be employed together with these. Preferred herbicide combinations are those with a synergistically active content of components (A), (B) and (C).

The herbicide combinations according to the invention preferably have synergistic effects. The synergistic effects are observed when the herbicides (A), (B) and (C) are applied together, but can frequently also be found when applied as a split application over time. Another possibility is to apply the individual herbicides or the herbicide combinations in several portions (sequential application), for example pre-emergence applications, followed by post-emergence applications or early post-emergence applications, followed by applications at medium or late post-emergence. Preferred is the simultaneous or nearly simultaneous application of the active ingredients of the herbicide combination according to the invention.

The synergistic effects allow reduction of the application rates of the individual active ingredients, a more potent action with the same application rate, the control of species to which no control has extended as yet (zero action), an extended application period and/or a reduced number of individual applications required and—as a result for the user—more advantageous weed control systems from the economical and ecological angle.

The herbicidal components of group (C1) act against monocotyledonous and dicotyledonous harmful plants. The herbicidal components of group (CII) act predominantly against dicotyledonous harmful plants, but can also be active against monocotyledonous harmful plants in some cases. The herbicidal components of group (CIII) act predominantly against monocotyledonous harmful plants, but can also be active against dicotyledonous harmful plants in some cases. The herbicidal components of group (CIV) are active against mono- and dicotyledonous harmful plants when employed in the nonselective field or in specifically tolerant crops.

The abovementioned formula (I) encompasses all stereoisomers and their mixtures, in particular also racemic mixtures and—if enantiomers are possible—the particular enantiomer which has a biological action. Compounds of the formula (I) and their salts and also their preparation are described, for example, in WO 95/29899. Examples of active ingredients of the formula (I) and their salts are N-[N-(4,6-dimethoxypyrimidin-2-yl)-aminocarbonyl]-2-(dimethylaminocarbonyl)-5-(formylamino) benzenesulfonamide (foramsulfuron, A1) and its salts such as the sodium salt (foramsulfuron-sodium, A2) (see, for example, AGROW No. 338, Oct. 15, 1999, page 26, PJB Publications Ltd. 1999).

The above formula (II) encompasses all stereoisomers and their mixtures, in particular also racemic mixtures, and—in as far as enantiomers are possible, all of the biologically active enantiomers. Compounds of the formula (II), their salts and their preparation are described, for example, in WO 92/13845. Examples of active compounds of the formula (II) and their salts are 3-(4-methoxy-6-methyl-1,3,5-triazin-2-yl)-1-(2-methoxycarbonyl-5-iodophenylsulfonyl)urea (iodosulfuron-methyl, B1) and its salts, such as the sodium salt (iodosulfuron-methyl-sodium, B2) (see, for example, WO 92/13845 and PM, pp. 547-548).

The abovementioned herbicides of the formulae (I) and (II) and their salts may inhibit the enzyme acetolactate synthase (ALS) and thus protein synthesis in plants. The application rate of the herbicides of the formulae (I) and (II) can vary within a wide range, for example between 0.001 and 0.5 kg of AS/ha. The abbreviation AS/ha used in this description means active substance per hectare, based on 100% active ingredient. In the case of applications at application rates of 0.01 to 0.1 kg of AS/ha of the herbicides of the formulae (I) and (II), preferably of the formulae (A1), (A2), (B1) or (B2), a relatively broad spectrum of annual and perennial broad-leaved weeds, grass weeds and cyperacea is controlled pre- and post-emergence. The application rates in the case of the combinations according to the invention are, as a rule, lower, e.g. in the range from 0.5 to 120 g of AS/ha, preferably 2 to 80 g of AS/ha.

As a rule, the active ingredients can be formulated as water-soluble wettable powders (WP), water-dispersible granules (WDG), water-emulsifiable granules (WEG), suspoemulsion (SE) or oil suspension concentrate (SC).

The quantitative ratios (A+B)/C which are generally used are stated hereinabove and identify the weight ratio of the two components (A+B) and C to each other. The weight ratio of the components A and B to each other is generally 1:50-1200:1, preferably 1:10-500:1.

For use of the active ingredients of the formulae (I) and (II) or their salts in plant crops, it is expedient, depending on the plant crop, to apply a safener from certain application rates upward in order to reduce or to avoid damage to the crop plants. Examples of suitable safeners are those which have a safener action in combination with sulfonylurea herbicides, preferably phenylsulfonylureas. Suitable safeners are disclosed in WO-A-96/14747 and the literature cited therein.

The following groups of compounds are examples of suitable safeners for the abovementioned herbicidal active ingredients (A) and (B):

a) Compounds of the dichlorophenylpyrazoline-3-carboxylic acid (S1 type), preferably compounds such as ethyl 1-(2,4-dichlorophenyl)-5-(ethoxycarbonyl)-5-methyl-2-pyrazoline-3-carboxylate (S1-1, mefenpyrdiethyl, PM, pp. 781-782), and related compounds as they are described in WO 91/07874.

b) Dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-d ichlorophenyl)-5-isopropylpyrazole-3-carboxylate (S1-3), ethyl 1-(2,4-dichlorophenyl)-5-(1,1-dimethyl-ethyl)pyrazole-3- carboxylate (S1-4), ethyl 1-(2,4-dichlorophenyl)-5-phenylpyrazole-3- carboxylate (S1-5) and related compounds as are described in EP-A-333 131 and EP-A-269 806.

c) Compounds of the triazolecarboxylic acid (S1) type, preferably compounds such as fenchlorazole, i.e. ethyl 1-(2,4-dichlorophenyl)-5-trichloromethyl-(1H)-1,2,4-triazole-3-carboxylate (S1-6) and related compounds (see EP-A-174 562 and EP-A-346 620).

d) Compounds of the 5-benzyl- or 5-phenyl-2-isoxazoline-3-carboxylic acid type or of the 5,5-diphenyl-2-isoxazoline-3-carboxylic acid type, preferably compounds such as ethyl 5-(2,4-dichlorobenzyl)-2- isoxazoline-3-carboxylate (S1-7) or ethyl 5-phenyl-2-isoxazoline-3-carboxylate (S1-8) and related compounds as are described in WO 91/08202, or of ethyl 5,5-diphenyl-2-isoxazolinecarboxylate (S1-9, isoxadifen-ethyl) or n-propyl 5,5-diphenyl-2-isoxazolinecarboxylate (S1-0) or ethyl 5-(4-!fluorophenyl)-5-phenyl-2-isoxazoline-3-carboxylate (S1-11), as are described in Patent Application (WO-A-95/07897).

e) Compounds of the 8-quinoline oxyacetic acid (S2) type, preferably 1-methylhex-1-yl (5-chloro-8-quinolinoxy)acetate (S2-1, cloquintocet-mexyl, e.g. PM, pp. 263-264),
(1,3-dimethyl but-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminooxy)-1-ethyl (5-chloro-8-quinolinoxy) acetate (S2-8), 2-oxoprop-1-yl (5-chloro-8-quinolinoxy) acetate (S2-9) and related compounds as are described in EP-A-8 750, EP-A-94 349 and EP-A-191 736 or EP-A-0 492 366.

f) Compounds of the (5-chloro-8-quinolinoxy)malonic acid type, preferably compounds such as diethyl (5-chloro-8-quinolinoxy)malonate, diallyl (5-chloro-8-qu inoli noxy)malonate, methyl ethyl (5-chloro-8-quinolinoxy)-malonate and related compounds as are described in EP-A-0 582 198.

g) Active ingredients of the phenoxyacetic acids, phenoxypropionic acids or aromatic carboxylic acids type, such as, for example, 2,4-dichlorophenoxyacetic acid (and esters) (2,4-D), 4-chloro-2-methylphenoxypropionic esters (mecoprop), MCPA or 3,6-dichloro-2-methoxybenzoic acid (and esters) (dicamba).

In many cases, the abovementioned safeners are also suitable for active ingredients of group (B). In addition, the following safeners are suitable for the herbicide combinations according to the invention:

h) active ingredients of the pyrimidine type, such as "fenclorim" (PM, pp. 512-511) (=4,6-dichloro-2-phenylpyrimidine), i) active ingredients of the dichloroacetamide type, which are.frequently used as pre-emergence safeners (soil-acting safeners) such as, for example, "dichloromid" (PM, pp. 363-364) (=N,N-diallyl-2,2-dichloroacetamide), "AR-29148" (=3-dichloroacetyl-2,2,5-trimethyl-1,3-oxazolidone by Stauffer), "benoxacor" (PM, pp. 102-103) (=4-dichloroacetyl-3,4-dihydro-3-methyl-2H-1,4-benzoxazine),
"APPG-1292" (=N-allyl-N[(1,3-dioxolan-2-yl)-methyl]dichloroacetamide by PPG Industries),
"ADK-24" (=N-allyl-N-[(allylaminocarbonyl)-methyl]-d ich loroacetamide by Sagro-Chem),
"AAD-67" or "AMON 4660)" (=3-dichloroacetyl-1-oxa-3-aza-spiro[4,5]decane by Nitrokemia or Monsanto), "diclonon" or "ABAS145138" or "ALAB145138" (=(=3-dichloroacetyl-2,5,5-trimethyl-1,3-diazabicyclo[4.3.0]nonane by BASF) and "furilazol" or "AMON 13900" (see PM, 637-638) (=(RS)-3-dichloroacetyl-5-(2-furyl)-2,2-dimethyloxazolidone)

j) active ingredients of the dichloroacetones type, such as, for example, "AMG 191" (CAS Reg. No. 96420-72-3) (=2-dichloromethyl-2-methyl-1,3-dioxolane by Nitrokemia), k) active ingredients of the oxyimino compounds type which are known as seed-dressing materials such as, for example, "oxabetrinil" (PM, pp. 902-903) (=(Z)-1,3-dioxolan-2-ylmethoxyimino(phenyl)acetonitrile), which is known as safener in seed dressing to prevent metolachlor damage, "fluxofenim" (PM, pp. 613-614) (=1-(4-chlorophenyl)-2,2,2-trifluoro-1-ethanone O-(1,3-dioxolan-2-ylmethyl)-oxime, which is known as safener in seed dressing to prevent metolachlor damage, and "cyometrinil" or "A-CGA-43089" (PM, p.1304) (=(Z)-cyanomethoxyimino(phenyl)acetonitrile), which is known as safener in seed dressing to prevent metolachlor damage, l) active ingredients of the thiazolecarboxylic esters type, which are known as seed-dressing materials, such as, for example, "flurazol" (PM, pp. 590-591) (=benzyl 2-chloro-4-trifluoromethyl-1,3-thiazole-5-carboxylate), which is known as safener in seed dressing to prevent alachlor and metolachlor damage, m) active ingredients of the naphthalenedicarboxylic acids type which are known as seed-dressing agents, such as, for example, "naphthalic anhydride" (PM, p.1342) (=1,8-naphthalenedicarboxylic anhydride), which is known as safener for maize in seed dressing to prevent thiocarbamate herbicide damage, n) active ingredients of the chromaneacetic acids type, such as, for example, "ACL 304415" (CAS Reg. No. 31541-57-8) (=2-84-carboxychroman-4-yl)acetic acid by American Cyanamid), o) active ingredients which, in addition to a herbicidal action against harmful plants, also have a safener action on crop plants, such as, for example, "dimepiperate" or AMY-93"(PM, pp.404-405) (=S-1-methyl-1-phenylethyl piperidine-1-carbothioate), "daimuron" or "ASK 23" (PM, p.330) (=1-(l-methyl-1-phenylethyl)-3-p-tolylurea), "cumyluron"="AJC-940" (=3-(2-chlorophenylmethyl)-1-(1-methyl-1-phenyl-ethyl) urea, see JP-A-60087254), "methoxyphenon" or "ANK 049" (=3,3'-dimethyl-4-methoxy-benzophenone), "CSB" (=1-bromo-4-(chloromethylsulfonyl)benzene) (CAS Reg. No. 54091-06-4 by Kumiai).

The herbicides (A) and (B) are suitable for controlling harmful plants in crops of plants, for example in economically important crops such as cereals (for example wheat, barley, rye, oats, rice, maize, sorghum and millet, sugar beet, sugar cane, oilseed rape, cotton and soya, in particular in maize, if appropriate in the presence of safeners (for example, the combination (A1)+(S1-9) is commercially available under the name Optiono and the combination (A1)+(B2)+(S1-9) under the name MaisTero). The above crops are also preferred for the combinations (A)+(B)+(C).

Also encompassed by the invention are those herbicide combinations which additionally contain one or more further agrochemical active compounds with a different structure, such as herbicides, insecticides, fungicides or safeners, besides the components (A), (B) and (C). If such combinations also contain the combinations (A)+(B)+(C) according to the invention, the preferred conditions mentioned hereinbelow, in particular for combinations (A)+(B)+(C) according to the invention, also mainly apply to such combinations with regard to the combination (A)+(B)+(C) in question.

Of particular interest is the application of herbicidal compositions which comprise the following compounds (A)+(B)+(C):

(A1)+(B1)+(C1), (A1)+(B1)+(C2), (A1)+(B1)+(C3), (A1)+(B1)+(C4), (A1)+(B1)+(C5), (A1)+(B1)+(C6), (A1)+(B1)+(C7), (A1)+(B1)+(C8), (A1)+(B1)+(C9), (A1)+(B1)+(C10), (A1)+(B1)+(C11), (A1)+(B1)+(C12), (A1)+(B1)+(C13), (A1)+(B1)+(C14), (A1)+(B1)+(C15), (A1)+(B1)+(C16), (A1)+(B1)+(C17), (A1)+(B1)+(C18), (A1)+(B1)+(C19), (A1)+(B1)+(C20), (A1)+(B1)+(C21), (A1)+(B1)+(C22), (A1)+(B1)+(C23), (A1)+(B1)+(C24), (A1)+(B1)+(C25), (A1)+(B1)+(C26), (A1)+(B1)+(C27), (A1)+(B1)+(C28), (A1)+(B1)+(C29), (A1)+(B1)+(C30), (A1)+(B1)+(C31), (A1)+(B1)+(C32), (A1)+(B1)+(C33), (A1)+(B1)+(C34),(A1)+(B1)+(C35),(A1)+(B1)+(C36), (A1)+(B1)+(C37), (A1)+(B1)+(C38), (A1)+(B1)+(C39), (A1)+(B1)+(C40), (A1)+(B1)+(C41),(A1)+(B1)+(C42),(A1)+(B1)+(C43),(A1)+(B1)+(C44),(A1)+(B1)+(C45),(A1)+(B1)+(C46),(A1)+(B1)+(C47),(A1)+(B1)+(C48),(A1)+(B1)+(C49), (A1)+(B1)+(C50), (A1)+(B1)+(C51), (A1)+(B1)+(052), (A1)+(B1)+(C53), (A1)+(B1)+(C54), (A1)+(B1)+(C55), (A1)+(B1)+(C56), (A1)+(B1)+(C57), (A1)+(B1)+(C58), (A1)+(B1)+(C59), (A1),+(B1)+(C60), (A1)+(B1)+(C61), (A1)+(B1)+(C62), (A1)+(B1)+(C63);

(A1)+(B2)+(C1), (A1)+(B2)+(C), (A1)+(B2)+(C3), (A1)+(B2)+(C4), (A1)+(B2)+(C5), (A1)+(B2)+(C6), (A1)+(B2)+(C7), (A1)+(B2)+(C8), (A1)+(B2)+(C9), (A1)+(B2)+(C10), (A1)+(B2)+(C11), (A1)+(B2)+(C12), (A1)+(B2)+(C13), (A1)+(B2)+(C14), (A1)+(B2)+(C15), (A1)+(B2)+(C16), (A1)+(B2)+(C17), (A1)+(B2)+(C18), (A1)+(B2)+(C19), (A1)+(B2)+(C20), (A1)+(B2)+(C21), (A1)+(B2)+(C22), (A1)+(B2)+(C23), (A1)+(B2)+(C24), (A1)+(B2)+(C25), (A1)+(B2)+(C26), (A1)+(B2)+(C27), (A1)+(B2)+(C28), (A1)+(B2)+(C29), (A1)+(B2)+(C30), (A1)+(B2)+(C31), (A1)+(B2)+(C32), (A1)+(B2)+(C33), (A1)+(B2)+(C34), (A1)+(B2)+(C35), (A1)+(B2)+(C36), (A1)+(B2)+(C37), (A1)+(B2)+(C38), (A1)+(B2)+(C39), (A1)+(B2)+(C40), (A1)+(B2)+(C41), (A1)+(B2)+(C42), (A1)+(B2)+(C43), (A1)+(B2)+(C44), (A1)+(B2)+(C45), (A1)+(B2)+(C46), (A1)+(B2)+(C47), (A1)+(B2)+(C48), (A1)+(B2)+(C49), (A1)+(B2)+(C50), (A1)+(B2)+(C51), (A1)+(B2)+(C52), (A1)+(B2)+(C53), (A1)+(B2)+(C54), (A1)+(B2)+(C55), (A1)+(B2)+(C56), (A1)+(B2)+(C57), (A1)+(B2)+(C58), (A1)+(B2)+(C59), (A1)+(B2)+(C60), (A1)+(B2)+(C61), (A1)+(B2)+(C62), (A1)+(B2)+(C63);

(A2)+(B1)+(C1), (A2)+(B1)+(C2), (A2)+(B1)+(C3), (A2)+(B1)+(C4), (A2)+(B1)+(C5), (A2)+(B1)+(C6), (A2)+(B1)+(C7), (A2)+(B1)+(C8), (A2)+(B1)+(C9),(A2)+(B1)+(C10),(A2)+(B1)+(C11),(A2)+(B1)+(C12),(A2)+(B1)+(C13), (A2)+(B1)+(C14), (A2)+(B1)+(C15), (A2)+(B1)+(C16), (A2)+(B1)+(C17), (A2)+(B1)+(C18), (A2)+(B1)+(C19), (A2)+(B1)+(C20), (A2)+(B1)+(C21), (A2)+(B1)+(C22), (A2)+(B1)+(C23), (A2)+(B1)+(C24), (A2)+(B1)+(C25), (A2)+(B1)+(C26), (A2)+(B1)+(C27), (A2)+(B1)+(C28), (A2)+(B1)+(C29), (A2)+(B1)+(C30), (A2)+(B1)+(C31), (A2)+(B1)+(C32), (A2)+(B1)+(C33), (A2)+(B1)+(C34), (A2)+(B1)+(C35), (A2)+(B1)+(C36), (A2)+(B1)+(C37), (A2)+(B1)+(C38), (A2)+(B1)+(C39), (A2)+(B1)+(C40), (A2)+(B1)+(C41), (A2)+(B1)+(C42), (A2)+(B1)+(C43), (A2)+(B1)+(C44), (A2)+(B1)+(C45), (A2)+(B1)+(C46), (A2)+(B1)+(C47), (A2)+(B1)+(C48), (A2)+(B1)+(C49), (A2)+(B1)+(C50), (A2)+(B1)+(C51), (A2)+(B1)+(C52), (A2)+(B1)+(C53), (A2)+(B1)+(C54), (A2)+(B1)+(C55), (A2)+(B1)+(C56), (A2)+(B1)+(C57), (A2)+(B1)+(C58), (A2)+(B1)+(C59), (A2)+(B1)+(C60), (A2)+(B1)+(C61), (A2)+(B1)+(C62), (A2)+(B1)+(C63);

(A2)+(B2)+(C1), (A2)+(B2)+(C2), (A2)+(B2)+(C3), (A2)+(B2)+(C4), (A2)+(B2)+(C5), (A2)+(B2)+(C6), (A2)+

(B2)+(C7), (A2)+(B2)+(C8), (A2)+(B2)+(C9), (A2)+(B2)+(C10), (A2)+(B2)+(C11), (A2)+(B2)+(C12), (A2)+(B2)+(C13), (A2)+(B2)+(C14), (A2)+(B2)+(C15), (A2)+(B2)+(C16), (A2)+(B2)+(C17), (A2)+(B2)+(C18), (A2)+(B2)+(C19), (A2)+(B2)+(C20), (A2)+(B2)+(C21), (A2)+(B2)+(C22), (A2)+(B2)+(C23), (A2)+(B2)+(C24), (A2)+(B2)+(C25), (A2)+(B2)+(C26), (A2)+(B2)+(C27), (A2)+(B2)+(C28), (A2)+(B2)+(C29), (A2)+(B2)+(C30), (A2)+(B2)+(C31), (A2)+(B2)+(C32), (A2)+(B2)+(C33), (A2)+(B2)+(C34), (A2)+(B2)+(C35), (A2)+(B2)+(C36), (A2)+(B2)+(C37), (A2)+(B2)+(C38), (A2)+(B2)+(C39), (A2)+(B2)+(C40), (A2)+(B2)+(C41), (A2)+(B2)+(C42), (A2)+(B2)+(C43), (A2)+(B2)+(C44), (A2)+(B2)+(C45), (A2)+(B2)+(C46), (A2)+(B2)+(C47), (A2)+(B2)+(C48), (A2)+(B2)+(C49), (A2)+(B2)+(C50), (A2)+(B2)+(C51), (A2)+(B2)+(052), (A2)+(B2)+(C53), (A2)+(B2)+(C54), (A2)+(B2)+(C55), (A2)+(B2)+(C56), (A2)+(B2)+(C57), (A2)+(B2)+(C58), (A2)+(B2)+(C59), (A2)+(B2)+(C60), (A2)+(B2)+(C61), (A2)+(B2)+(C62), (A2)+(B2)+(C63);

(A1)+(A2)+(B1)+(B2)+(C1),(A1)+(A2)+(B1)+(B2)+(C2),(A1)+(A2)+(B1)+(B2)+(C3), (A1)+(A2)+(B1)+(B2)+(C4), (A1)+(A2)+(B1)+(B2)+(C5), (A1)+(A2)+(B1)+(B2)+(C6), (A1)+(A2)+(B1)+(B2)+(C7), (A1)+(A2)+(B1)+(B2)+(C8), (A1)+(A2)+(B1)+(B2)+(C9), (A1)+(A2)+(B1)+(B2)+(C10), (A1)+(A2)+(B1)+(B2)+(C11), (A1)+(A2)+(B1)+(B2)+(C12), (A1)+(A2)+(B1)+(B2)+(C13), (A1)+(A2)+(B1)+(B2)+(C14), (A1)+(A2)+(B1)+(B2)+(C15), (A1)+(A2)+(B1)+(B2)+(C16), (A1)+(A2)+(B1)+(B2)+(C17), (A1)+(A2)+(B1)+(B2)+(C18),(A1)+(A2)+(B1)+(B2)+(C19),(A1)+(A2)+(B1)+(B2)+(C20), (A1)+(A2)+(B1)+(B2)+(C21), (A1)+(A2)+(B1)+(B2)+(C22), (A1)+(A2)+(B1)+(B2)+(C23), (A1)+(A2)+(B1)+(B2)+(C24), (A1)+(A2)+(B81)+(B2)+(C25), (A1)+(A2)+(B1)+(B2)+(C26), (A1)+(A2)+(B1)+(B2)+(C27), (A1)+(A2)+(B1)+(B2)+(C28), (A1)+(A2)+(B1)+(B2)+(C29), (A1)+(A2)+(B1)+(B2)+(C30),(A1)+(A2)+(B1)+(B2)+(C31),(A1)+(A2)+(B1)+(B2)+(C32),(A1)+(A2)+(B1)+(B2)+(C33),(A1)+(A2)+(B1)+(B2)+(C34), (A1)+(A2)+(B1)+(B2)+(C35), (A1)+(A2)+(B1)+(B2)+(C36), (A1)+(A2)+(B1)+(B2)+(C37), (A1)+(A2)+(B1)+(B2)+(C38), (A1)+(A2)+(B1)+(B2)+(C39), (A1)+(A2)+(B1)+(B2)+(C40), (A1)+(A2)+(B1)+(B2)+(C41), (A1)+(A2)+(B1)+(B2)+(C42),(A1)+(A2)+(B1)+(B2)+(C43),(A1)+(A2)+(B1)+(B2)+(C44), (A1)+(A2)+(B1)+(B2)+(C45), (A1)+(A2)+(B1)+(B2)+(C46), (A1)+(A2)+(B1)+(B2)+(C47), (A1)+(A2)+(B1)+(B2)+(C48), (A1)+(A2)+(B1)+(B2)+(C49), (A1)+(A2)+(B1)+(B2)+(C50), (A1)+(A2)+(B1)+(B2)+(C51), (A1)+(A2)+(B1)+(B2)+(C52), (A1)+(A2)+(B1)+(B2)+(C53), (A1)+(A2)+(B1)+(B2)+(C54),(A1)+(A2)+(B1)+(B2)+(C55),(A1)+(A2)+(B1)+(B2)+(C56), (A1)+(A2)+(B1)+(B2)+(C57), (A1)+(A2)+(B1)+(B2)+(c58), (A1)+(A2)+(B1)+(B2)+(C59), (A1)+(A2)+(B1)+(B2)+(C60), (A1)+(A2)+(B1)+(B2)+(C61), (A1)+(A2)+(B1)+(B2)-+(C62), (A1)+(A2)+(B1)+(B2)+(C63).

In addition, each of the abovementioned herbicide combinations may additionally also contain one or more safeners, in particular a safener such as mefenpyr-diethyl (S1-1), isoxadifen-ethyl (S1-9) and cloquintocet-methyl (S2-1). In this context, the abovementioned ranges of the application rates, and application ratios, are preferred in each case. Examples are the herbicide combinations mentioned hereinbelow.

(A1)+(B1)+(C1)+(S1-1), (A1)+(B1)+(C2)+(S1-l), (A1)+(B1)+(C3)+(S1-1), (A1)+(B1)+(C4)+(S1-1), (A1)+(B1)+(C5)+(S1-1), (A1)+(B1)+(C6)+(S1-1), (A1)+(B1)+(C7)+(S1-1), (A1)+(B1)+(C8)+(S1-1), (A1)+(B1)+(C9)+(S1-1), (A1)+(B1)+(C10)+(S1-1), (A1)+(B1)+(C1)+(S1-1), (A1)+(B1)+(C12)+(S1-1), (A1)+(B1)+(C13)+(S1-1), (A1)+(B1)+(Ci4)+(S1-1); (A1)+(B1)+(C15)+(S1-1), (A1)+(B1)+(Ci6)+(S1-1), (A1)+(B1)+(C17)+(S1-1), (A1)+(B1)+(C18)+(S1-1), (A1)+(B1)+(C19)+(S1-1), (A1)+(B1)+(C20)+(S1-1), (A1)+(B1)+(C21)+(S1-1),(A1)+(B1)+(C22)+(S1-1),(A1)+(B1)+(C23)+(S1-1), (A1)+(B1)+(C24)+(S1-1), (A1)+(B1)+(C25)+(S1-1), (A1)+(B1)+(C26)+(S1-1), (A1)+(B1)+(C27)+(S1-1), (A1)+(B1)+(C28)+(S1-1), (A1)+(B1)+(C29)+(S1-1), (A1)+(B1)+(C30)+(S1-1), (A1)+(B1)+(C31)+(S1-1), (A1)+(B1)+(C32)+(S1-1), (A1)+(B1)+(C33)+(S1-1), (A1)+(B1)+(C34)+(S1-1), (A1)+(B1)+(C35)+(S1-1), (A1)+(B1)+(C36)+(S1-1), (A1)+(B1)+(C37)+(S1-1), (A1)+(B1)+(C38)+(S1-1), (A1)+(B1)+(C39)+(S1-1), (A1)+(B1)+(C40)+(S1-1), (A1)+(B1)+(C41)+(S1-1), (A1)+(B1)+(C42)+(S1-1), (A1)+(B1)+(C43)+(S1-1), (A1)+(B1)+(C44)+(S1-1), (A1)+(B1)+(C45)+(S1-1),(A1)+(B1)+(C46)+(S1-1),(A1)+(B1)+(C47)+(S1-1),(A1)+(B1)+(C48)+(S1-1),(A1)+(B1)+(C49)+(S1-1), (A1)+(B1)+(C50)+(S1-1),(A1)+(B1)+(C51)+(S1-1), (A1)+(B1)+(C52)+(S1-1), (A1)+(B1)+(C53)+(S1-1), (A1)+(B1)+(C54)+(S1-1), (A1)+(B1)+(C55)+(S1-1), (A1)+(B1)+(C56)+(S1-1), (A1)+(B1)+(C57)+(S1-1), (A1)+(B1)+(C58)+(S1-1), (A1)+(B1)+(C59)+(S1-1), (A1)+(B1)+(C60)+(S1-1), (A1)+(B1)+(C61)+(S1-1), (A1)+(B1)+(C62)+(S1-1),(A1)+(B1)+(C63)+(S1-1);

(A1)+(B2)+(C1)+(S1-1),(A1)+(B2)+(C)+(S1-1),(A1)+(B2)+(C3)+(S1-1), (A1)+(B2)+(C4)+(S1-1), (A1)+(B2)+(C5)+(S1-1), (A1)+(B2)+(C6)+(S1-1), (A1)+(B2)+(C7)+(S1-1), (A1)+(B2)+(C8)+(S1-1), (A1)+(B2)+(C9)+(S1-1), (A1)+(B2)+(C10)+(S1-1),(A1)+(B2)+(C1)+(S1-1),(A1)+(B2)+(C12)+(S1-1), (A1)+(B2)+(C13)+(S1-1), (A1)+(B2)+(C14)+(S1-1), (A1)+(B2)+(C15)+(S1-1), (A1)+(B2)+(C16)+(S1-1), (A1)+(B2)+(C17)+(S1-1), (A1)+(B2)+(C08)+(S1-1), (A1)+(B2)+(Ci9)+(S1-1), (A1)+(B2)+(C20)+(S1-1), (A1)+(B2)+(C21)+(S1-1), (A1)+(B2)+(C22)+(S1-1), (A1)+(B2)+(C23)+(S1-1), (A1)+(B2)+(C24)+(S1-1), (A1)+(B2)+(C25)+(S1-1), (A1)+(B2)+(C26)+(S1-1), (A1)+(B2)+(C27)+(S1-1), (A1)+(B2)+(C28)+(S1-1), (A1)+(B2)+(C29)+(S1-1)), (A1)+(B2)+(C30)+(S1-1), (A1)+(B2)+(C31)+(S1-1), (A1)+(B2)+(C32)+(S1-1), (A1)+(B2)+(C33)+(S1-1), (A1)+(B2)+(C34)+(S1-1), (A1)+(B2)+(C35)+(S1-1), (A1)+(B2)+(C36)+(S1-1), (A1)+(B2)+(C37)+(S1-1), (A1)+(B2)+(C38)+(S1-1), (A1)+(B2)+(C39)+(S1-1), (A1)+(B2)+(C40)+(S1-1), (A1)+(B2)+(C41)+(S1-1), (A1)+(B2)+(C42)+(S1-1), (A1)+(B2)+(C43)+(S1-1), (A1)+(B2)+(C44)+(S1-1), (A1)+(B2)+(C45)+(S1-1), (A1)+(B2)+(C46)+(S1-1), (A1)+(B2)+(C47)+(S1-1)), (A1)+(B2)+(C48)+(S1-1), (A1)+(B2)+(C49)+(S1-1), (A1)+(B2)+(C50)+(S1-1), (A1)+(B2)+(C51)+(S1-1), (A1)+(B2)+(C52)+(S1-1), (A1)+(B2)+(C53)+(S1-1), (A1)+(B2)+(C54)+(S1-1), (A1)+(B2)+(C55)+(S1-1), (A1)+(B2)+(C56)+(S1-1),(A1)+(B2)+(C57)+(S1-1),(A1)+(B2)+(C58)+(S1-1),(A1)+(B2)+(C59)+(S1-1), (A1)+(B2)+(C60)+(S1-1), (A1)+(B2)+(C61)+(S1-1), (A1)+(B2)+(C62)+(S1-1), (A1)+(B2)+(C63)+(S1-1);

(A2)+(B1)+(C1)+(S1-1), (A2)+(B1)+(C2)+(S1-1), (A2)+(B1)+(C3)+(S1-1), (A2)+(B1)+(C4)+(S1-1),(A2)+(B1)+(C5)+(S1-1),(A2)+(B1)+(C6)+(S1-1), (A2)+(B1)+(C7)+(S1-1), (A2)+(B1)+(C8)+(S1-1), (A2)+(B1)+(C9)+(S1-1), (A2)+(B1)+(C10)+(S1-1), (A2)+(B1)+(C11)+(S1-1), (A2)+(B1)+(C12)+(S1-1), (A2)+(B1)+(C13)+(S1-1), (A2)+(B1)+(C14)+(S1-1), (A2)+(B1)+(C15)+(S1-1), (A2)+(B1)+(C16)+(S1-1), (A2)+(B1)+(C17)+(S1-1), (A2)+(B1)+(C18)+(S1-1),(A2)+(B1)+(C19)+(S1-1),(A2)+(B1)+(C20)+(S1-1)), (A2)+(B1)+(C21)+(S1-1), (A2)+(B1)+(C22)+(S1-1)), (A2)+(B1)+(C23)+(S1-1), (A2)+(B1)+(C24)+(S1-1), (A2)+(B1)+(C25)+(S1-1), (A2)+(B1)+(C26)+(S1-1), (A2)+(B1)+(C27)+(S1-1), (A2)+(B1)+(C28)+(S1-1), (A2)+(B1)+(C29)+(S1-1), (A2)+(B1)+(C30)+(S1-1), (A2)+(B1)+(C31)#(S1-1), (A2)+(B1)+(C32)+(S1-1),(A2)+(B1)+(C33)+(S1-1),(A2)+(B1)+(C34)+(S1-1), (A2)+(B1)+(C35)+(S1-1), (A2)+(B1)+(C36)+(S1-1), (A2)+(B1)+(C37)+(S1-1), (A2)+(B1)+(C38)+(S1-1), (A2)+(B1)+(C39)+(S1-1), (A2)+(B1)+(C40)+(S1-1), (A2)+(B1)+(C41)+(S1-1), (A2)+(B1)+(C42)+(S1-1), (A2)+(B1)+(C43)+(S1-1), (A2)+(B1)+(C44)+(S1-1), (A2)+(B1)+(C45)+(S1-1),(A2)+(B1)+(C46)+(S1-1),(A2)+(B1)+(C47)+(S1-1),(A2)+(B1)+(C48)+(S1-1), (A2)+(B1)+(C49)+(S1-1), (A2)+(B1)+(C50)+(S1-1), (A2)+(B1)+(C51)+(S1-1),(A2)+(B1)+(C52)+(S1-1), (A2)+(81)+(C53)+(S1-1), (A2)+(B1)+(C54)+(S1-1), (A2)+(B1)+(C55)+(S1-1), (A2)+(B1)+(C56)+(S1-1), (A2)+(B1)+(C57)+(S1-1), (A2)+(B1)+(C58)+(S1-1), (A2)+(B1)+(C59)+(S1-1), (A2)+(B1)+(C60)+(S1-1), (A2)+(B1)+(C61)+(S1-1),(A2)+(B1)+(C62)+(S1-1), (A2)+(B1)+(C63)+(S1-1);

(A2)+(B2)+(C1)+(S1-1), (A2)+(B2)+(C2)+(S1-1), (A2)+(B2)+(C3)+(S1-1), (A2)+(B2)+(C4)+(S1-1), (A2)+(B2)+(C5)+(S1-1), (A2)+(B2)+(C6)+(S1-1), (A2)+(B2)+(C7)+(S1-1), (A2)+(B2)+(C8)+(S1-1), (A2)+(B2)+(C9)+(S1-1), (A2)+(B2)+(C10)+(S1-1), (A2)+(B2)+(C1)+(S1-1), (A2)+(B2)+(C12)+(S1-1),(A2)+(B2)+(C03)+(S1-1),(A2)+(B2)+(ql4)+(S1-1),(A2)+(B2)+(C15)+(S1-1), (A2)+(B2)+(C16)+(S1-1), (A2)+(B2)+(C17)+(S1-1), (A2)+(B2)+(C18)+(S1-1), (A2)+(B2)+(C19)+(S1-1), (A2)+(B2)+(C20)+(S1-1), (A2)+(B2)+(C21)+(S1-1), (A2)+(B2)+(C22)+(S1-1), (A2)+(B2)+(C23)+(S1-1), (A2)+(B2)+(C24)+(S1-1), (A2)+(B2)+(C25)+(S1-1), (A2)+(B2)+(C26)+(S1-1), (A2)+(B2)+(C27)+(S1-1), (A2)+(B2)+(C28)+(S1-1),..(A2)+(B2)+(C29)+(S1-1), (A2)+(B2)+(C30)+(S1-1), (A2)+(B2)+(C31)+(S1-1), (A2)+(B2)+(C32)+(S1-1), (A2)+(B2)+(C33)+(S1-1), (A2)+(B2)+(C34)+(S1-1), (A2)+(B2)+(C35)+(S1-1), (A2)+(B2)+(C36)+(S1-1), (A2)+(B2)+(C37)+(S1-1), (A2)+(B2)+(C38)+(S1-1), (A2)+(B2)+(C39)+(S1-1), (A2)+(B2)+(C40)+(S1-1), (A2)+(B2)+(C41)+(S1-1), (A2)+(B2)+(C42)+(S1-1), (A2)+(B2)+(C43)+(S1-1), (A2)+(B2)+(C44)+(S1-1), (A2)+(B2)+(C45)+(S1-1), (A2)+(B2)+(C46)+(S1-1), (A2)+(B2)+(C47)+(S1-1), (A2)+(B2)+(C48)+(S1-1),(A2)+(B2)+(C49)+(S1-1),(A2)+(B2)+(C50)+(S1-1),(A2)+(B2)+(C51)+(S1-1), (A2)+(B2)+(C52)+(S1-1), (A2)+(B2)+(C53)+(S1-1), (A2)+(B2)+(C54)+(S1-1), (A2)+(B2)+(C55)+(S1-1), (A2)+(B2)+(C56)+(S1-1), (A2)+(B2)+(C57)+(S1-1), (A2)+(B2)+(C58)+(S1-1), (A2)+(B2)+(C59)+(S1-1), (A2)+(B2)+(C60)+(S1-1), (A2)+(B2)+(C61)+(S1-1), (A2)+(B2)+(C62)+(S1-1), (A2)+(B2)+(C63)+(S1-1);

(A1)+(A2)+(B1)+(B2)+(C1)+(S1-1)),(A1)+(A2)+(B1)+(B2)+(C2)+(S1-1), (A1)+(A2)+(B1)+(B2)+(C3)+(S1-1), (A1)+(A2)+(B1)+(B2)+(C4)+(S1-1), (A1)+(A2)+(B1)+(B2)+(C5)+(S1-1), (A1)+(A2)+(B1)+(B2)+(C6)+(S1-1), (A1)+(A2)+(B1)+(B2)+(C7)+(S1-1), (A1)+(A2)+(B1)+(B2)+(C8)+(S1-1), (A1)+(A2)+(B1)+(B2)+(C9)+(S1-1), (A1)+(A2)+(B1)+(B2)+(C10)+(S1-1), (A1)+(A2)+(B1)+(B2),+(C1)+(S1-1), (A1)+(A2)+(B1)+(B2)+(C12)+(S1-1), (A1)+(A2)+(B1)+(B2)+(C13)+(S1-1),(A1)+(A2)+(B1)+(B2)+(C14)+(S1-1)),(A1)+(A2)+(B1)+(B2)+(C15)+(S1-1), (A1)+(A2)+(B1)+(B2)+(C16)+(S1-1), (A1)+(A2)+(B1)+(B2)+(C17)+(S1-1), (A1)+(A2)+(B1)+(B2)+(C18)+(S1-1), (A1)+(A2)+(B1)+(B2)+(C19)+(S1-1), (A1)+(A2)+(B1)+(B2)+(C20)+(S1-1), (A1)+(A2)+(B1)+(B2)+(C21)+(S1-1), (A1)+(A2)+(B1)+(B2)+(C22)+(S1-1), (A1)+(A2)+(B1)+(B2)+(C23)+(S1-1), (A1)+(A2)+(B1)+(B2)+(C24)+(S1-1), (A1)+(A2)+(B1)+(B2)+(C25)+(S1-1),(A1)+(A2)+(B1)+(B2)+(C26)+(S1-1), (A1)+(A2)+(B1)+(B2)+(C27)+(S1-1), (A1)+(A2)+(B1)+(B2)+(C28)+(S1-1), (A1)+(A2)+(B1)+(B2)+(C29)+(S1-1), (A1)+(A2)+(B1)+(B2)+(C30)+(S1-1), (A1)+(A2)+(B1)+(B2)+(C31)+(S1-1), (A1)+(A2)+(B1)+(B2)+(C32)+-(S1-), (A1)+(A2)+(B1)+(B2)+(C33)+(S1-1), (A1)+(A2)+(B1)+(B2)+(C34)+(S1-1),(A1)+(A2)+(B1)+(B2)+(C35)+(S1-1), (A1)+(A2)+(B1)+(B2)+(C36)+(S1-1), (A1)+(A2)+(B1)+(B2)+(C37)+(S1-1), (A1)+(A2)+(B1)+(B2)+(C38)+(S1-1), (A1)+(A2)+(B1)+(B2)+(C39)+(S1-1), (A1)+(A2)+(B1)+(B2)+(C40)+(S1-1), (A1)+(A2)+(B1)+(B2)+(C41)+(S1-1),(A1)+(A2)+(B1)+(B2)+(C42)+(S1-1), (A1)+(A2)+(B1)+(B2)+(C43)+(S1-1),(A1)+(A2)+(B1)+(B2)+(C44)+(S1-1)),(A1)+(A2)+(B1)+(B2)+(C45)+(S1-1), (A1)+(A2)+(B1)+(B2)+(C46)+(S1-1), (A1)+(A2)+(B1)+(B2)+(C47)+(S1-1), (A1)+(A2)+(B1)+(B2)+(C48)+(S1-1), (A1)+(A2)+(B1)+(B2)+(C49)+(S1-1), (A1)+(A2)+(B1)+(B2)+(C50)+(S1-1), (A1)+(A2)+(B1)+(B2)+(C51)+(S1-1), (A1)+(A2)+(B1)+(B2)+(C52)+(S1-1), (A1)+(A2)+(B1)+(B2)+(C53)+(S1-1),(A1)+(A2)+(B1)+(B2)+(C54)+(S1-1)), (A1)+(A2)+(B1)+(B2)+(C55)+(S1-1), (A1)+(A2)+(B1)+(B2)+(C56)+(S1-1), (A1)+(A2)+(B1)+(B2)+(C57)+(S1-1), (A1)+(A2)+(B1)+(B2)+(C58)+(S1-1), (A1)+(A2)+(B1)+(B2)+(C59)+(S1-1), (A1)+(A2)+(B1)+(B2)+(C60)+(S1-1), (A1)+(A2)+(B1)+(B2)+(C61)+(S1-1), (A1)+(A2)+(B1)+(B2)+(C62)+(S1-1),(A1)+(A2)+(B1)+(B2)+(C63)+(S1-1).

(A1)+(B1)+(C1)+(S1-9),(A1)+(B1)+(C2)+(S1-9),(A1)+(B1)+(C3)+(S1-9), (A1)+(B1)+(C4)+(S1-9), (A1)+(B1)+(C5)+(S1-9), (A1)+(B1)+(C6)+(S1-9), (A1)+(B1)+(C7)+(S1-9), (A1)+(B1)+(C8)+(S1-9), (At)+(B1)+(C9)+(S1-9), (A1)+(B1)+(C10)+(S1-9), (A1)+(B1)+(C11)+(S1-9), (A1)+(B1)+(C12)+(S1-9), (A1)+(B1)+(C13)+(S1-9), (A1)+(B1),+(C14)+(S1-9), (A1)+(B1)+(C15)+(S1-9), (A1)+(B1)+(C16)+(S1-9), (A1)+(B1)+(C17)+(S1-9), (A1)+(B1)+(C18)+(S1-9), (A1)+(B1)+(C19)+(S1-9), (A1)+(B1)+(C20)+(S1-9), (A1)+(B1)+(C21)+(S1-9), (A1)+(B1)+(C22)+(S1-9), (A1)+(B1)+(C23)+(S1-9), (A1)+(B1)+(C24)+(S1-9), (A1)+(B1)+(C25)+(S1-9), (A1)+(B1)+(C26)+(S1-9), (A1)+(B1)+(C27)+(S1-9), (A1)+(B1)+(C28)+(S1-9), (A1)+(B1)+(C29)+(S1-9),(A1)+(B1)+(C30)+(S1-9),(A1)+(B1)+(C31)+(S1-9), (A1)+(B1)+(C32)+(S1-9), (A1)+(B1)+(C33)+(S1-9), (A1)+(B1)+(C34)+(S1-9), (A1)+(B1)+(C35)+(S1-9), (A1)+(B1)+(C36)+(S1-9), (A1)+(B1)+(C37)+(S1-9), (A1)+(B1)+(C38)+(S1-9), (A1)+(B1)+(C39)+(S1-9), (A1)+(B1)+(C40)+(S1-9), (A1)+(B1)+(C41)+(S1-9), (A1)+(B1)+(C42)+(S1-9), (A1)+(B1)+(C43)+(S1-9), (A1)+(B1)+(C44)+(S1-9), (A1)+(B1)+(C45)+(S1-9), (A1)+(B1)+(C46)+(S1-9), (A1)+(B1)+(047)+(S1-9), (A1)+(B1)+(C48)+(S1-9), (A1)+(B1)+(C49)+(S1-9), (A1)+(B1)+(C50)+(S1-9), (A1)+(B1)+(C51)+(S1-9), (A1)+(B1)+(C52)+(S1-9), (A1)+(B1)+(C53)+(S1-9), (A1)+(B1)+(C54)+(S1-9), (A1)+(B1)+(C55)+(S1-9), (A1)+(B1)+(C56)+(S1-9), (A1)+(B1)+(C57)+(S1-9), (A1)+(B1)+(C58)+(S1-9), (A1)+(B1)+(C59)+(S1-9), (A1)+(B1)+(C60)+(S1-9), (A1)+(B1)+(C61)+(S1-9), (A1)+(B1)+(C62)+(S1-9), (A1)+(B1)+(C63)+(S1-9);

(A1)+(B2)+(C1)+(S1-9), (A1)+(B2)+(C)+(S1-9), (A1)+(B2)+(C3)+(S1-9), (A1)+(B2)+(C4)+(S1-9), (A1)+(B2)+(C5)+(S1-9), (A1)+(B2)+(C6)+(S1-9), (A1)+(B2)+(C7)+(S1-9), (A1)+(B2)+(C8)+(S1-9), (A1)+(B2)+(C9)+.(S1-9), (A1)+(B2)+(C10)+(S1-9), (A1)+(B2)+(C11)+(S1-9), (A1)+(B2)+(C12)+(S1-9), (A1)+(B2)+(C13)+(S1-9), (A1)+(B2)+(C14)+(S1-9), (A1)+(B2)+(C15)+(S1-9), (A1)+(B2)+(C16)+(S1-9), (A1)+(B2)+(C17)+(S1-9), (A1)+(B2)+(C18)+(S1-9), (A1)+(B2)+(C19)+(S1-9), (A1)+(B2)+(C20)+(S1-9), (A1)+(B2)+(C21)+(S1-9), (A1)+(B2)+(C22)+(S1-9), (A1)+(B2)+(C23)+(S1-9), (A1)+(B2)+(C24)+(S1-9), (A1)+(B2)+(C25)+(S1-9), (A1)+(B2)+

(C26)+(S1-9), (A1)+(B2)+(C27)+(S1-9), (A1)+(B2)+(C28)+(S1-9), (A1)+(B2)+(C29)+(S1-9), (A1)+(B2)+(C30)+(S1-9), (A1)+(B2)+(C31)+(S1-9), (A1)+(B2)+(C32)+(S1-9), (A1)+(B2)+(C33)+(S1-9), (A1)+(B2)+(C34)+(S1-9), (A1)+(B2)+(C35)+(S1-9), (A1)+(B2)+(C36)+(S1-9), (A1)+(B2)+(C37)+(S1-9), (A1)+(B2)+(C38)+(S1-9), (A1)+(B2)+(C39)+(S1-9), (A1)+(B2)+(C40)+(S1-9), (A1)+(B2)+(C41)+(S1-9), (A1)+(B2)+(C42)+(S1-9), (A1)+(B2)+(C43)+(S1-9), (A1)+(B2)+(C44)+(S1-9), (A1)+(B2)+(C45)+(S1-9), (A1)+(B2)+(C46)+(S1-9), (A1)+(B2)+(C47)+(S1-9), (A1)+(B2)+(C48)+(S1-9), (A1)+(B2)+(C49)+(S1-9), (A1)+(B2)+(C50)+(S1-9), (A1)+(B2)+(C51)+(S1-9), (A1)+(B2)+(C52)+(S1-9), (A1)+(B2)+(C53)+(S1-9), (A1)+(B2)+(C54)+(S1-9), (A1)+(B2)+(C55)+(S1-9), (A1)+(B2)+(C56)+(S1-9), (A1)+(B2)+(C57)+(S1-9), (A1)+(B2)+(C58)+(S1-9), (A1)+(B2)+(C59)+(S1-9), (A1)+(B2)+(C60)+(S1-9), (A1)+(B2)+(C61)+(S1-9), (A1)+(B2)+(C62)+(S1-9), (A1)+(B2)+(C63)+(S1-9);

(A2)+(B1)+(C1)+(S1-9), (A2)+(B1)+(C2)+(S1-9), (A2)+(B1)+(C3)+(S1-9), (A2)+(B1)+(C4)+(S1-9), (A2)+(B1)+(C5)+(S1-9), (A2)+(B1)+(C6)+(S1-9), (A2)+(B1)+(C7)+(S1-9),(A2)+(B1)+(C8)+(S1-9),(A2)+(B1)+(C9)+(S1-9), (A2)+(B1)+(C10)+(S1-9),(A2)+(B1)+(C11)+(S1-9),(A2)+(B1)+(C12)+(S1-9),(A2)+(B1)+(C13)+(S1-9),(A2)+(B1)+(C14)+(S1-9),(A2)+(B1)+(C15)+(S1-9), (A2)+(B1)+(C16)+(S1-9), (A2)+(B1)+(C17)+(S1-9), (A2)+(B1)+(C18)+(S1-9), (A2)+(B1)+(C19)+(S1-9), (A2)+(B1)+(C20)+(S1-9), (A2)+(B1)+(C21)+(S1-9), (A2)+(B1)+(C22)+(S1-9), (A2)+(B1)+(C23)+(S1-9), (A2)+(B1)+(C24)+(S1-9), (A2)+(B1)+(C25)+(S1-9), (A2)+(B1)+(C26)+(S1-9), (A2)+(B1)+(C27)+(S1-9), (A2)+(B1)+(C28)+(S1-9), (A2)+(B1)+(C29)+(S1-9), (A2)+(B1)+(C30)+(S1-9), (A2)+(B1)+(C31)+(S1-9), (A2)+(B1)+(C32)+(S1-9), (A2)+(B1)+(C33)+(S1-9), (A2)+(B1)+(C34)+(S1-9), (A2)+(B1)+(C35)+(S1-9), (A2)+(B1)+(C36)+(S1-9), (A2)+(B1)+(C37)+(S1-9), (A2)+(B1)+(C38)+(S1-9), (A2)+(B1)+(C39)+(S1-9), (A2)+(B1)+(C40)+,(S1-9),(A2)+(B1)+(C41)+(S1-9),(A2)+(B1)+(C42)+(S1-9), (A2)+(B1)+(C43)+(S1-9), (A2)+(B1)+(C44)+(S1-9), (A2)+(B1)+(C45)+(S1-9), (A2)+(B1)+(C46)+(S1-9), (A2)+(B1)+(C47)+(S1-9), (A2)+(B1)+(C48)+(S1-9), (A2)+(B1)+(C49)+(S1-9), (A2)+(B1)+(C50)+(S1-9), (A2)+(B1)+(C51)+(S1-9), (A2)+(B1)+(C52)+(S1-9), (A2)+(B1)+(C53)+(S1-9), (A2)+(B1)+(C54)+(S1-9), (A2)+(B1)+(C55)+(S1-9), (A2)+(B1)+(C56)+(S1-9), (A2)+(B1)+(C57)+(S1-9), (A2)+(B1)+(C58)+(S1-9), (A2)+(B1)+(C59)+(S1-9),(A2)+(B1)+(C60)+(S1-9),(A2)+(B1)+(C61)+(S1-9),(A2)+(B1)+(C62)+(S1-9), (A2)+(B1)+(C63)+(S 1-9);

(A2)+(B2)+(C1)+(S1-9), (A2)+(B2)+(C2)+(S1-9), (A2)+(B2)+(C3)+(S1-9), (A2)+(B2)+(C4)+(S1-9), (A2)+(B2)+(C5)+(S1-9), (A2)+(B2)+(C6)+(S1-9), (A2)+(B2)+(C7)+(S1-9), (A2)+(B2)+(C8)+(S1-9), (A2)+(B2)+(C9)+(S1-9), (A2)+(B2)+(C10)+(S1-9), (A2)+(B2)+(C11)+(S1-9), (A2)+(B2)+(C12)+(S1-9), (A2)+(B2)+(C13)+(S1-9), (A2)+(B2)+(C14)+(S1-9), (A2)+(B2)+(C15)+(S1-9), (A2)+(B2)+(C6)+(S1-9), (A2)+(B2)+(C7)+(S1-9), (A2)+(B2)+(C18)+(S1-9), (A2)+(B2)+(C19)+(S1-9), (A2)+(B2)+(C20)+(S1-9), (A2)+(B2)+(C21)+(S1-9), (A2)+(B2)+(C22)+(S1-9), (A2)+(B2)+(C23)+(S1-9), (A2)+(B2)+(C24)+(S1-9), (A2)+(B2)+(C25)+(S1-9), (A2)+(B2)+(C26)+(S1-9), (A2)+(B2)+(C27)+(S1-9), (A2)+(B2)+(C28)+(S1-9), (A2)+(B2)+(C29)+(S1-9), (A2)+(B2)+(C30)+(S1-9), (A2)+(B2)+(C31)+(S1-9), (A2)+(B2)+(C32)+(S1-9), (A2)+(B2)+(C33)+(S1-9), (A2)+(B2)+(C34)+(S1-9), (A2)+(B2)+(C35)+(S1-9), (A2)+(B2)+(C36)+(S1-9), (A2)+(B2)+(C37)+(S1-9), (A2)+(B2)+(C38)+(S1-9), (A2)+(B2)+(C39)+(S1-9), (A2)+(B2)+(C40)+(S1-9), (A2)+(B2)+(C41)+(S1-9), (A2)+(B2)+(C42)+(S1-9), (A2)+(B2)+(C43)+(S1-9), (A2)+(B2)+(C44)+(S1-9), (A2)+(B2)+(C45)+(S1-9),,(A2)-+(B2)+(C46)+(S1-9), (A2)+(B2)+(C47)+(S1-9), (A2)+(B2)+(C48)+(S1-9), (A2)+(B2)+(C49)+(S1-9), (A2)+(B2)+(C50)+(S1-9), (A2)+(B2)+(C51)+(S1-9), (A2)+(B2)+(C52)+(S1-9), (A2)+(B2)+(C53)+(S1-9), (A2)+(B2)+(C54)+(S1-9), (A2)+(B2)+(C55)+(S1-9), (A2)+(B2)+(C56)+(S1-9), (A2)+(B2)+(C57)+(S1-9), (A2)+(B2)+(C58)+(S1-9), (A2)+(B2)+(C59)+(S1-9), (A2)+(B2)+(C60)+(S1-9), (A2)+(B2)+(C61)+(S1-9), (A2)+(B2)+(C62)+(S1-9), (A2)+(B2)+(C63)+(S1-9); (A1)+(A2)+(B1)+(B2)+(C1)+(S1-9),(A1)+(A2)+(B)+(B2)+(C2)+(S1-9), (A1)+(A2)+(B1)+(B2)+(C3)+(S1-9), (A1)+(A2)+(B1)+(B2)+(C4)+(S1-9), (A1)+(A2)+(B1)+(B2)+(C5)+(S1-9), (A1)+(A2)+(B1)+(B2)+(C6)+(S1-9), (A1)+(A2)+(B1)+(B2)+(C7)+(S1-9), (A1)+(A2)+(B1)+(B2)+(C8)+(S1-9), (A1)+(A2)+(B1)+(B2)+(C9)+(S1-9),(A1)+(A2)+(B1)+(B2)+(C10)+(S1-9), (A1)+(A2)+(B1)+(B2)+(C11)+(S1-9), (A1)+(A2)+(B1)+(B2)+(C12)+(S1-9),(A1)+(A2)+(B1)+(B2)+(C13)+(S1-9),(A1)+(A2)+(B1)+(B2)+(C14)+(S1-9), (A1)+(A2)+(B1)+(B2)+(C5)+(S1-9), (A1)+(A2)+(B1)+(B2)+(C16)+(S1-9), (A1)+(A2)+(B1)+(B2)+(C17)+(S1-9), (A1)+(A2)+(B1)+(B2)+(C18)+(S19),(A1)+(A2)+(B1)+(B2)+(C19)+(S1-9),(A1)+(A2)+(B1)+(B2)+(C20)+(S1-9), (A1)+(A2)+(B1)+(B2)+(C21)+(S1-9), (A1)+(A2)+(B1)+(B2)+(C22)+(S1-9), (A1)+(A2)+(B)+(B2)+(C23)+(S1-9), (A1)+(A2)+(B1)+(B2)+(C24)+(S1-9), (A1)+(A2)+(B1)+(B2)+(C25)+(S1-9), (A1)+(A2)+(B1)+(B2)+(C26)+(S1-9), (A1)+(A2)+(B1)+(B2)+(C27)+(S1-9), (A1)+(A2)+(B1)+(B2)+(C28)+(S1-9),(A1)+(A2)+(B1)+(B2)+(C29)+(S1-9),(A1)+(A2)+(B1)+(B2)+(C30)+(S1-9), (A1)+(A2)+(B1)+(B2)+(C31)+(S1-9), (A1)+(A2)+(B1)+(B2)+(C32)+(S1-9), (A1)+(A2)+(B1)+(B2)+(C33)+(S1-9), (A1)+(A2)+(B1)+(B2)+(C34)+(S1-9), (A1)+(A2)+(B1)+(B2)+(C35)+(S1-9), (A1)+(A2)+(B1)+(B2)+(C36)+(S1-9), (A1)+(A2)+(B1)+(B2)+(C37)+(S1-9), (A1)+(A2)+(B1)+(B2)+(C38)+(S1-9), (A1)+(A2)+(B1)+(B2)+(C39)+(S1-9), (A1)+(A2)+(B1)+(B2)+(C40)+(S1-9), (A1)+(A2)+(B1)+(B2)+(C41)+(S1-9), (A1)+(A2)+(B1)+(B2)+(C42)+(S1-9), (A1)+(A2)+(B1)+(B2)+(C43)+(S1-9), (A1)+(A2)+(B1)+(B2)+(C44)+(S1-9), (A1)+(A2)+(B1)+(B2)+(C45)+(S1-9), (A1)+(A2)+(B1)+(B2)+(C46)+(S1-9), (A1)+(A2)+(B1)+(B2)+(C47)+(S1-9),(A1)+(A2)+(B1)+(B2)+(C48)+(S1-9),(A1)+(A2)+(B1)+(B2)+(C49)+(S1-9), (A1)+(A2)+(B1)+(B2)+(C50)+(S1-9),-(A1)+(A2)+(B1)+(B2)+(C51)+(S1-9), (A1)+(A2)+(B1)+(B2)+(C52)+(S1-9), (A1)+(A2)+(B1)+(B2)+(C53)+(S1-9), (A1)+(A2)+(B1)+(B2)+(C54)+(S1-9), (A1)+(A2)+(B1)+(B2)+(C55)+(S1-9), (A1)+(A2)+(B1)+(B2)+(C56)+(S1-9), (A1)+(A2)+(B1)+(B2)+(C57)+(S1-9),(A1)+(A2)+(B1)+(B2)+(C58)+(S1-9), (A1)+(A2)+(B1)+(B2)+(C59)+(S1-9), (A1)+(A2)+(B1)+(B2)+(C60)+(S1-9), (A1)+(A2)+(B1)+(B2)+(C61)+(S1-9), (A1)+(A2)+(B)+(B2)+(C62)+(S1-9), (A1)+(A2)+(B1).+(B2)+(C63)+(S1-9).

(A1)+(B1)+(C1)+(S2-1),(A1)+(B1)+(C2)+(S2-1), (A1)+(B1)+(C3)+(S2-1), (A1)+(B1)+(C4)+(S2-1), (A1)+(B1)+(C5)+(S2-1), (A1)+(B1)+(C6)+(S2-1), (A1)+(B1)+(C7)+(S2-1), (A1)+(B1)+(C8)+(S2-1), (A1)+(B1)+(C9)+(S2-1), (A1)+(B1)+(C10)+(S2-1), (A1)+(B1)+(C11)+(S2-1), (A1)+(B1)+(C12)+(S2-1), (A1)+(B1)+(C13)+(S2-1), (A1)+(B1)+(C14)+(S2-1), (A1)+(B1)+(C15)+(S2-1), (A1)+(B1)+(C16)+(S2-1), (A1)+(B1)+(C17)+(S2-1), (A1)+(B1)+(C18)+(S2-1),(A1)+(B1)+(C19)+(S2-1),(A1)+(B1)+(C20)+(S2-1), (A1)+(B1)+(C21)+(S2-1), (A1)+.(B1)+(C22)+(S2-1), (A1)+(B1)+(C23)+(S2-1), (A1)+(B1)+(C24)+(S2-1), (A1)+(B1)+(C25)+(S2-1), (A1)+(B1)+(C26)+(S2-1), (A1)+(B1)+(C27)+(S2-1), (A1),+(B1)+(C28)+(S2-1), (A1)+(B1)+(C29)+(S2-1), (A1)+(B1)+(C30)+(S2-1), (A1)+(B1)+(C31)+(S2-1), (A1)+(B1)+(C32)+(S2-1), (A1)+(B1)+(C33)+(S2-1), (A1)+(B1)+(C34)+(S2-1), (A1)+(B1)+(C35)+(S2-1), (A1)+(B1)+(C36)+(S2-1), (A1)+(B1)+(C37)+(S2-1), (A1)+(B1)+(C38)+(S2-1), (A1)+(B1)+(C39)+(S2-1), (A1)+(B1)+(C40)+(S2-1), (A1)+(B1)+(C41)+(S2-1), (A1)+(B1)+(C42)+(S2-1), (A1)+(B1)+(C43)+(S2-1), (A1)+(B1)+(C44)+(S2-1), (A1)+(B1)+(C45)+(S2-1), (A1)+(B1)+(C46)+(S2-1), (A1)+(B1)+(C47)+(S2-1), (A1)+(B1)+(C48)+(S2-1), (A1)+(B1)+(C49)+(S2-1), (A1)+(B1)+(C50)+(S2-1), (A1)+(B1)+(C51)+(S2-1), (A1)+(B1)+(C52)+(S2-1), (A1).+(B1)+(C53)+(S2-1), (A1)+(B1)+(C54)+(S2-1), (A1)+(B1)+(C55)+(S2-1), (A1)+(B1)+(C56)+(S2-1), (A1)+(B1)+(C57)+(S2-1), (A1)+(B1)+(C58)+(S2-1), (A1)+(B1)+(C59)+(S2-1), (A1)+(B1)+(060)+(S2-1), (A1)+(B1)+(C61)+(S2-1), (A1)+(B1)+(C62)+(S2-1), (A1)+(B1)+(C63)+(S2-1);

(A1)+(B2)+(C1)+(S2-1), (A1)+(B2)+(C)+(S2-1), (A1)+(B2)+(C3)+(S2-1), (A1)+(B2)+(C4)+(S2-1), (A1)+(B2)+(C5)+(S2-1), (A1)+(B2)+(C6)+(S2-1), (A1)+(B2)+(C7)+(S2-1), (A1)+(B2)+(C8)+(S2-1), (A1)+(B2)+(C9)+(S2-1), (A1)+(B2)+(C10)+(S2-1), (A1)+(B2)+(C11)+(S2-1), (A1)+(B2)+(C12)+(S2-1), (A1)+(B2)+(C13)+(S2-1), (A1)+(B2)+(C14)+(S2-1), (A1)+(B2)+(C15)+(S2-1), (A1)+(B2)+(C16)+(S2-1), (A1)+(B2)+(C17)+(S2-1), (A1)+(B2)+(C18)+(S2-1), (A1)+(B2)+(C19)+(S2-1), (A1)+(B2)+(C20)+(S2-1), (A1)+(B2)+(C21)+(S2-1), (A1)+(B2)+(C22)+(S2-1), (A1)+(B2)+(C23)+(S2-1), (A1)+(B2)+(C24)+(S2-1), (A1)+(B2)+(C25)+(S2-1), (A1)+(B2)+(C26)+(S2-1), (A1)+(B2)+(C27)+(S2-1), (A1)+(B2)+(C28)+(S2-1), (A1)+(B2)+(C29)+(S2-1), (A1)+(B2)+(C30)+(S2-1), (A1)+(B2)+(C31)+(S2-1), (A1)+(B2)+(C32)+(S2-1), (A1)+(B2)+(C33)+(S2-1), (A1)+(B2)+(C34)+(S2-1), (A1)+(B2)+(C35)+(S2-1), (A1)+(B2)+(C36)+(S2-1), (A1)+(B2)+(C37)+(S2-1), (A1)+(B2)+(C38)+(S2-1), (A1)+(B2)+(C39)+(S2-1), (A1)+(B2)+(C40)+(S2-1), (A1)+(B2)+(C41)+(S2-1), (A1)+(B2)+(C42)+(S2-1), (A1)+(B2)+(C43)+(S2-1), (A1)+(B2)+(C44)+(S2-1), (A1)+(B2)+(C45)+(S2-1), (A1)+(B2)+(C46)+(S2-1), (A1)+(B2)+(C47)+(S2-1), (A1)+(B2)+(C48)+(S2-1), (A1)+(B2)+(C49)+(S2-1), (A1)+(B2)+(C50)+(S2-1), (A1)+(B2)+(C51)+(S2-1), (A1)+(B2)+(C52)+(S2-1), (A1)+(B2)+(C53)+(S2-1), (A1)+(B2)+(C54)+(S2-1), (A1)+(B2)+(C55)+(S2-1), (A1)+(B2)+(C56)+(S2-1), (A1)+(B2)+(C57)+(S2-1), (A1)+(B2)+(C58)+(S2-1), (A1)+(B2)+(C59)+(S2-1), (A1)+(B2)+(C60)+(S2-1), (A1)+(B2)+(C61)+(S2-1), (A1)+(B2)+(C62)+(S2-1), (A1)+(B2)+(C63)+(S2-1);

(A2)+(B1)+(C1)+(S2-1), (A2)+(B1)+(C2)+(S2-1), (A2)+(B1)+(C3)+(S2-1), (A2)+(B1)+(C4)+(S2-1), (A2)+(B1)+(C5)+(S2-1), (A2)+(B1)+(C6)+(S2-1), (A2)+(B1)+(C7)+(S2-1), (A2)+(B1)+(C8)+(S2-1), (A2)+(B1)+(C9)+(S2-1), (A2)+(B1)+(C10)+(S2-1), (A2)+(B1)+(C11)+(S2-1), (A2)+(B1)+(C12)+(S2-1), (A2)+(B1)+(C13)+(S2-1), (A2)+(B1)+(C14)+(S2-1), (A2)+(B1)+(C15)+(S2-1), (A2)+(B1)+(C16)+(S2-1), (A2)+(B1)+(C17)+(S2-1), (A2)+(B1)+(C18)+(S2-1), (A2)+(B1)+(C19)+(S2-1), (A2)+(B1)+(C20)+(S2-1), (A2)+(B1)+(C21)+(S2-1), (A2)+(B1)+(C22)+(S2-1), (A2)+(B1)+(C23)+(S2-1), (A2)+(B1)+(C24)+(S2-1), (A2-)+(B1)+(C25)+(S2-1), (A2)+(B)+(C26)+(S2-1), (A2)+(B1)+(C27)+(S2-1), (A2)+(B1)+(C28)+(S2-1), (A2)+(B1)+(C29)+(S2-1), (A2)+(B1)+(C30)+(S2-1), (A2)+(B1)+(C31)+(S2-1), (A2)+(B1)+(C32)+(S2-1), (A2)+(B1)+(C33)+(S2-1), (A2)+(B1)+(C34)+(S2-1), (A2)+(B1)+(C35)+(S2-1), (A2)+(B1)+(C36)+(S2-1), (A2)+(B1)+(C37)+,(S2-1), (A2)+(B1)+(C38)+(S2-1), (A2)+(B1)+(C39)+(S2-1), (A2)+(B1)+(C40)+(S2-1), (A2)+(B1)+(C41)+(S2-1), (A2)+(B1)+(C42)+(S2-1), (A2)+(B1)+(C43)+(S2-1), (A2)+(B1)+(C44)+(S2-1), (A2)+(B1)+(C45)+(S2-1), (A2)+(B1)+(C46)+(S2-1), (A2)+(B1)+(C47)+(S2-1), (A2)+(B1)+(C48)+(S2-1), (A2)+(B1)+(C49)+(S2-1), (A2)+(B1)+(C50)+(S2-1), (A2)+(B1)+(C51)+(S2-1), (A2)+(B1)+(C52)+(S2-1), (A2)+(B1)+(C53)+(S2-1), (A2)+(B1)+(C54)+(S2-1), (A2)+(B1)+(C55)+(S2-1), (A2)+(B1)+(C56)+(S2-1), (A2)+(B1)+(C57)+(S2-1), (A2)+(B1)+(C58)+(S2-1), (A2)+(B1)+(C59)+(S2-1), (A2)+(B1)+(C60)+(S2-1), (A2)+(B1)+(C61)+(S2-1), (A2)+(B1)+(C62)+(S2-1), (A2)+(B1)+(C63)+(S2-1);

(A2)+(B2)+(C1)+(S2-1), (A2)+(B2)+(C2)+(S2-1), (A2)+(B2)+(C3)+(S2-1), (A2)+(B2)+(C4)+(S2-1), (A2)+(B2)+(C5)+(S2-1), (A2)+(B2)+(C6)+(S2-1), (A2)+(B2)+(C7)+(S2-1), (A2)+(B2)+(C8)+(S2-1), (A2)+(B2)+(C9)+(S2-1), (A2)+(B2)+(C10)+(S2-1), (A2)+(B2)+(C11)+(S2-1), (A2)+(B2)+(C12)+(S2-1), (A2)+(B2)+(C13)+(S2-1), (A2)+(B2)+(C14)+(S2-1), (A2)+(B2)+(C15)+(S2-1), (A2)+(B2)+(C16)+(S2-1), (A2)+(B2)+(C17)+(S2-1), (A2)+(B2)+(C18)+(S2-1), (A2)+(B2)+(C19)+(S2-1), (A2)+(B2)+(C20)+(S2-1) (A2)+(B2)+(C21)+(S2-1), (A2)+(B2)+(C22)+(S2-1), (A2)+(B2)+(C23)+(S2-1), (A2)+(B2)+(C24)+(S2-1), (A2)+(B2)+(C25)+(S2-1), (A2)+(B2)+(C26)+(S2-1), (A2)+(B2)+(C27)+(S2-1), (A2)+(B2)+(C28)+(S2-1), (A2)+(B2)+(C29)+(S2-1), (A2)+(B2)+(C30)+(S2-1), (A2)+(B2)+(C31)+(S2-1), (A2)+(B2)+(C32)+(S2-1), (A2)+(B2)+(C33)+(S2-1), (A2)+(B2)+(C34)+(S2-1), (A2)+(B2)+(C35)+(S2-1), (A2)+(B2)+(C36)+(S2-1), (A2)+(B2)+(C37)+(S2-1), (A2)+(B2)+(C38)+(S2-1), (A2)+(B2)+(C39)+(S2-1), (A2)+(B2)+(C40)+(S2-1), (A2)+(B2)+(C41)+(S2-1), (A2)+(B2)+(C42)+(S2-1), (A2)+(B2)+(C43)+(S2-1), (A2)+(B2)+(C44)+(S2-1), (A2)+(B2)+(C45)+(S2-1), (A2)+(B2)+(C46)+(S2-1), (A2)+(B2)+(C47)+(S2-1), (A2)+(B2)+(C48)+(S2-1), (A2)+(B2)+(C49)+(S2-1), (A2)+(B2)+(C50)+(S2-1), (A2)+(B2)+(C51)+(S2-1), (A2)+(B2)+(C52)+.(S2-1), (A2)+(B2)+(C53)+(S2-1), (A2)+(B2)+(C54)+(S2-1), (A2)+(B2)+(C55)+(S2-1), (A2)+(B2)+(C56)+(S2-1), (A2)+(B2)+(C57)+(S2-1), (A2)+(B2)+(C58)+(S2-1), (A2)+(B2)+(C59)+(S2-1), (A2)+(B2)+(C60)+(S2-1), (A2)+(B2)+(C61)+(S2-1), (A2)+(B2)+(C62)+(S2-1), (A2)+(B2)+(C63)+(S2-1);

(A1)+(A2)+(B1)+(B2)+(C1)+(S2-1), (A1)+(A2)+(B1)+(B2)+(C2)+(S2-1), (A1)+(A2)+(B1)+(B2)+(C3)+(S2-1), (A1)+(A2)+(B1)+(B2)+(C4)+(S2-1), (A1)+(A2)+(B1)+(B2)+(C5)+(S2-1), (A1)+(A2)+(B1)+(B2)+(C6)+(S2-1), (A1)+(A2)+(B1)+(B2)+(C7)+(S2-1), (A1)+(A2)+(B1)+(B2)+(C8)+(S2-1), (A1)+(A2)+(B1)+(B2)+(C9)+(S2-1), (A1)+(A2)+(B1)+(B2)+(C10)+(S2-1), (A1)+(A2)+(B1)+(B2)+(C11)+(S2-1), (A1)+(A2)+(B1),+(B2)+(C12)+(S2-1), (A1)+(A2)+(B1)+(B2)+(C13)+(S2-1),(A1)+(A2)+(B1)+(B2)+(C14)+(S2-1), (A1)+(A2)+(B1)+(B2)+(C15)+(S2-1), (A1)+(A2)+(B1)+(B2)+(C16)+(S2-1), (A1)+(A2)+(B1)+(B2)+(C17)+(S2-1), (A1)+(A2)+(B1)+(B2)+(C18)+(S2-1), (A1)+(A2)+(B1)+(B2)+(C19)+(S2-1), (A1)+(A2)+(B1)+(B2)+(C20)+(S2-1), (A1)+(A2)+(B1)+(B2)+(C21)+(S2-1), (A1)+(A2)+(B1)+(B2)+(C22)+(S2-1), (A1)+(A2)+(B1)+(B2)+(C23)+(S2-1), (A1)+(A2)+(B1)+(B2)+(C24)+(S2-1), (A1)+(A2)+(B1)+(B2)+(C25)+(S2-1), (A1)+(A2)+(B1)+(B2)+(C26)+(S2-1), (A1)+(A2)+(B1)+(B2)+(C27)+(S2-1), (A1)+(A2)+(B1)+(B2)+(C28)+(S2-1), (A1)+(A2)+(B1)+(B2)+(C29)+(S2-1), (A1)+(A2)+(B1)+(B2)+(C30)+(S2-1), (A1)+(A2)+(B1)+(B2)+(C31)+(S2-1),(A1)+(A2)+(B1)+

(B2)+(C32)+(S2-1), (A1)+(A2)+(B1)+(B2)+(C33)+(S2-1), (A1)+(A2)+(B1)+(B2)+(C34)+(S2-1), (A1)+(A2)+(B1)+(B2)+(C35)+(S2-1), (A1)+(A2)+(B1)+(B2)+(C36)+(S2-1), (A1)+(A2)+(B1)+(B2)+(C37)+(S2-1), (A1)+(A2)+(B1)+(B2)+(C38)+(S2-1), (A1)+(A2)+(B1)+(B2)+(C39)+(S2-1), (A1)+(A2)+(B1)+(B2)+(C40)+(S2-1), (A1)+(A2)+(B1)+(B2)+(C41)+(S2-1), (A1)+(A2)+(B1)+(B2)+(C42)+(S2-1), (A1)+(A2)+(B1)+(B2)+(C43)+(S2-1), (A1)+(A2)+(B1)+(B2)+(C44)+(S2-1), (A1)+(A2)+(B1)+(B2)+(C45)+(S2-1), (A1)+(A2)+(B1)+(B2)+(C46)+(S2-1), (A1)+(A2)+(B1)+(B2)+(C47)+(S2-1), (A1)+(A2)+(B1)+(B2)+(C48)+(S2-1), (A1)+(A2)+(B1)+(B2)+(C49)+(S2-1), (A1)+(A2)+(B1)+(B2)+(C50)+(S2-1), (A1)+(A2)+(B1)+(B2)+(C51)+(S2-1), (A1)+(A2)+(B1)+(B2)+(C52)+(S2-1), (A1)+(A2)+(B1)+(B2)+(C53)+(S2-1), (A1)+(A2)+(B1)+(B2)+(C54)+(S2-1), (A1)+(A2)+(B1)+(B2)+(C55)+(S2-1), (A1)+(A2)+(B1)+(B2)+(C56)+(S2-1), (A1)+(A2)+(B1)+(B2)+(C57)+(S2-1), (A1)+(A2)+(B1)+(B2)+(C58)+(S2-1), (A1)+(A2)+(B1)+(B2)+(C59)+(S2-1), (A1)+(A2)+(B1)+(B2)+(C60)+(S2-1), (A1)+(A2)+(B1)+(B2)+(C61)+(S2-1), (A1)+(A2)+(B1)+(B2)+(C62)+(S2-1), (A1)+(A2)+(B1)+(B2)+(C63)+(S2-1).

It may make sense to combine one or more herbicides (A) with one or more herbicides (B) and one or more herbicides (C), for example one herbicide (A) with one herbicide (B) and one or more herbicide (C). Herbicide combinations according to the invention, which contain more than one herbicide (C), are, for example, those which contain the following herbicide combinations as component (C): C3 +C7, C2 +C7, C3 +C10, C5 +C7, C3 +C10 +C33, C20 +C37, C7 +C15 +C16 +C39, C15 +C16 +C25 +C39, C16 +C41, C10 +C36, C10 +C33, C10 +C34, C33 +C34, C33+ C42, C23 +C24, C3 +C7 +C36, C3 +C7 +C18 or C3 +C10 +C15, where the preferred component (A) and (B) which is present is the compounds (A1)+(B1), (A1)+(B2), (A2)+(B1) or (A2)+(B2), in particular (A1)+(B2), and where a safener such as (S1-1), (S1-9) or (S2-1), in particular (S1-9) may additionally be present. Furthermore, the combinations according to the invention may be employed together with other agrochemical active compounds, for example from the group of the safeners, fungicides, insecticides and plant growth regulators, or additives and formulation auxiliaries conventionally used in crop protection. Additives are, for example, fertilizers and colorants. The ranges of application rates and the application ratios mentioned above are preferred in each case in this context.

The combinations according to the invention (=herbicidal compositions) have an outstanding herbicidal activity against a broad spectrum of economically important monocotyledonous and dicotyledonous harmful plants. The active ingredients also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compounds according to the invention, without the enumeration being a restriction to certain species.

Examples of weed species on which the herbicidal compositions act efficiently are, from amongst the monocotyledonous weed species, Avena spp., Alopecurus spp:, Apera spica venti, Brachiaria spp., Digitaria spp., Lolium spp., Equinochloa spp., Panicum spp., Phalaris spp., Poa spp., Setaria spp. and Cyperus species from the annual group, and, amongst the perennial species, Agropyron, Cynodon, Imperata and Sorghum and also perennial Cyperus species.

In the case of the dicotyledonous weed species, the spectrum of action extends to species such as, for example, Abutilon spp., Amaranthus spp., Chenopodium spp., Chrysanthemum spp., Galium spp., Ipomoea spp., Kochia spp., Lamium spp., Matricaria spp., Pharbitis spp., Polygonum spp., Sida spp., Sinapis spp., Solanum spp., Stellaria spp., Veronica spp. and Viola spp., Xanthium spp., amongst the annuals, and Convolvulus, Cirsium, Rumex and Artemisia in the case of the perennial weeds.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active ingredients are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rainfastness of the active ingredients in the combinations according to the invention is advantageous. A particular advantage is that the dosages of the compounds (A), (B) and (C) which are used in the combinations and are effective, can be adjusted to such a low quantity that their soil action is optimally low. This does not only allow them to be employed in sensitive crops in the first place, but groundwater contaminations are virtually avoided. The active-ingredient combination according to the invention allows the application rate of the active ingredients required to be reduced considerably.

When herbicides of the type (A)+(B)+(C) are used jointly, superadditive (=synergistic) effects are observed in a preferred embodiment. This means that the effect in the combinations exceeds the expected total of the effects of the individual herbicides employed. The synergistic effects allow the application rate to be reduced, a broader spectrum of broad-leaved weeds and grass weeds to be controlled, the herbicidal action to take place more rapidly, the duration of action to be longer, the harmful plants to be controlled better while using only one, or few, applications, and the application period which is possible to be extended. In some cases, use of the compositions also reduces the amount of harmful constituents, such as nitrogen or oleic acid, and their entry into the ground.

The abovementioned properties and advantages are necessary for weed control practice to keep agricultural crops free from undesired competing plants and thus to guarantee and/or increase the yields from the qualitative and quantitative point of view. These novel combinations markedly exceed the technical state of the art with a view to the properties described.

While the combinations according to the invention have an outstanding herbicidal activity against monocotyledonous and dicotyledonous weeds, the crop plants are damaged only to a minor extent, if at all.

Moreover, some of the compositions according to the invention have outstanding growth-regulatory properties on the crop plants. They engage in the plants metabolism in a regulatory manner and can thus be employed for provoking directed effects on plant constituents and to facilitate harvesting such as for example by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions according to the invention can be employed for controlling harmful plants in genetically modified crop plants or crop plants obtained by mutation/selection. These crop plants are distinguished as a mole by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding methods and the generation of mutants,(see, for example, U.S. Pat. Nos. 5,162,602; 4,761,373; 4,443,971). Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to other herbicides, for example to sulfonylureas (EP-A-0257993, US-A-5013659), transgenic crop plants with the capability of producing Bacillus thuringiensis toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated: see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone", VCH Weinheim 2nd Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribosome which specifically cleaves transcripts of the abovementioned gene product.

To this end, it is possible to use, on the one hand, DNA molecules which encompass the entire coding sequence of a gene product inclusive of any flanking sequences which may be present, as well as DNA molecules which only encompass portions of the coding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J.1 (1991), 95-106).

The transgenic plant cells can be regenerated by known techniques to give rise to intact plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired-vegetation (e.g. harmful plants), preferably in plant crops such as cereals (e.g. wheat, barley, rye, oats, hybrids thereof, such as triticale, rice, corn, panic grasses), sugar beet, sugar cane, oilseed rape, cotton and soya beans, preferably in corn, which comprises applying, together or separately, for example pr6-emergence, postemergence or pre- and post-emergence, one or more herbicides of type (A) together with one or more herbicides of type (B) and one or more herbicides of type (C), to the plants, e.g. the harmful plants, parts of these plants, seeds of these plants, or the area on which the plants grow, for example the area under cultivation.

The plant crops can also have been genetically modified or been obtained by mutation/selection and are preferably tolerant to acetolactate synthase (ALS) inhibitors.

The invention also relates to the use of the novel combinations of compounds (A)+(B)+(C) for controlling harmful plants, preferably in plant crops.

The active ingredient combinations according to the invention can exist not only as mixed formulations of the components (A), (B) and (C), if appropriate together with further agrochemically active ingredients, additives and/or customary formulation auxiliaries, which are then applied in the customary manner as a dilution with water, but also as so-called tank mixes by jointly diluting the separately formulated, or partially separately formulated, components with water.

The compounds (A), (B) and (C) or their combinations can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil- or water-based dispersions, suspoemulsions, dusts (DP), seed-dressing materials, granules for soil application or for broadcasting, or water-dispersible granules (WG), ULV formulations, microcapsules or waxes.

The individual formulation types are known in principle and are described for example, in: Winnacker-Küchler, "Chemische Technologie", Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Dariand Books, Caldwell N.J.; H.v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesellschaft, Stuttgart 1976, Winnacker-Kuchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active ingredient, also comprise ionic or nonionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutyinaphthalenesulfonate or else sodium oleoylmethyltauride, in addition to a diluent or inert material.

Emulsifiable concentrates are prepared by dissolving the active ingredient in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active ingredient with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active ingredient onto adsorptive, granulated inert material or by applying active ingredient concentrates to the surface of carriers such as sand, kaolites or granulated inert material with the aid of binders, for example polyvinyl alcohol, sodium polyacrylate or else mineral oils. Suitable active ingredients may also be granulated in the manner conventionally used for the production of fertilizer granules, if desired in a mixture with fertilizers. As a rule, water-dispersible granules are prepared by conventional processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

As regards further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise 0.1 to 99 percent by weight, in particular 2 to 95% by weight, of active ingredients of the types A, B and/or C, the following concentrations being customary, depending on the type of formulation: The active ingredient concentration in wettable powders is, for example, approximately 10 to 95% by weight, the remainder to 100% by weight being composed of customary formulation constituents. In the case of emulsifiable concentrates, the active ingredient concentration may amount to, for example, 5 to 80% by weight. Formulations in the form of dusts comprise, in most cases, 5 to 20% by weight of active ingredient, sprayable solutions approximately 0.2 to 25% by weight of active ingredient.

In the case of granules such as dispersible granules, the active ingredient content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active ingredient formulations may comprise, if appropriate, the conventional adhesives, wetters, dispersants, emulsifiers, preservatives, antifreeze agents, solvents, fillers, colorants, carriers, antifoams, evaporation inhibitors, pH regulators or viscosity regulators. The herbicidal activity of the herbicide combinations according to the invention can be improved, for example by surface-active substances, preferably by wetting agents from the series of the fatty alcohol polyglycol ethers. The fatty alcohol polyglycol ethers preferably have 10-18 carbon atoms in the fatty alcohol residue and 2-20 ethylene oxide units in the polyglycol ether moiety. The fatty alcohol polyglycol ethers may exist in nonionic form or else in ionic form, for example in the form of fatty alcohol polyglycol ether sulfates, which are used, for example, in the form of the alkali metal salts (for example the sodium and potassium salts) or the ammonium salts, or else in the form of the alkaline earth metal salts, such as magnesium salts, such as the sodium salt of $C_{12}/C_{14}$-fatty alcohol diglycol ether sulfate (Genapol® LRO, Clariant GmbH); see, for example, EP-A-0476555, EP-A-0048436, EP-A-0336151 or U.S. Pat. No. 4,400,196 and Proc. EWRS Symp. "Factors affecting herbicidal activity and selectivity", 227-232 (1988). Examples of non-ionic fatty alcohol polyglycol ethers are ($C_{10}$-$C_{18}$), preferably ($C_{10}$-$C_{14}$)-fatty alcohol polyglycol ethers which contain 2-20, preferably 3-15, ethylene oxide units (for example isotridecyl alcohol polyglycol ether), such as Genapol® X-030, Genapol® X-060, Genapol® X-080 or Genapol® X-150 (all by Clariant GmbH).

The present invention furthermore encompasses the combination of herbicides (A), (B) and (C) with the abovementioned wetting agents from the series of the fatty alcohol polyglycol ethers which preferably contain 10-18 carbon atoms in the fatty alcohol residue and 2-20 ethylene oxide units in the polyglycol ether moiety and which can be present in nonionic or ionic form (for example in the form of the fatty alcohol polyglycol ether sulfates). Preferred are the sodium salt of $C_{12}$/C14-fatty alcohol diglycol ether sulfate (Genapol® LRO, Clariant GmbH) and isotridecyl alcohol polyglycol ethers having 3-15 ethylene oxide units, for example from the Genapol® X series, such as Genapol® X-030, Genapol® X-060, Genapol(® X-080 and Genapol® X-150 (all by Clariant GmbH). It is furthermore known that fatty alcohol polyglycol ethers such as nonionic or ionic fatty alcohol polyglycol ethers (for example fatty alcohol polyglycol ether sulfates) are also suitable as penetrants and synergists for a series of other herbicides, inter alia also for herbicides from the series of the imidazolinones (see, for example, EP-A-0502014).

The herbicidal activity can also be increased by using vegetable oils. The term vegetable oils is to be understood as meaning oils from oil-plant species, such as soya oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids as they exist, for example, in oils from oil-plant species, or $C_1$-$C_{20}$-alkyl-$C_{10}$-$C_{22}$-fatty acid esters as can be obtained, for example, by transesterification of the abovementioned glycerol- or glycol-$C_{10}$-$C_{22}$-fatty acid esters with $C_1$-$C_{20}$-alcohols (for example methanol, ethanol, propanol or butanol). Transesterification can be carried out by known methods as are described, for example, in Rompp Chemie Lexikon, 9th Edition, Volume 2, page 1343, Thieme Verlag Stuttgart.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fafty acid esters are the uniform or mixed glycol esters and glycerol esters of $C_{10}$-$C_{22}$-fatty acids, in particular of those fatty acids which have an even number of carbon atoms, for example erucic acid, lauric acid, palmitic acid and, in particular, $C_{18}$-fatty acids such as stearic acid, oleic acid, linolic acid or linolenic acid.

The vegetable oils can be present in the herbicidal compositions according to the invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

In a further embodiment, the present invention encompasses combinations of herbicides (A), (B) and (C) with the abovementioned vegetable oils, such as rapeseed oil, preferably in the form of commercially available oil-containing formulation additives, in particular those which are based on rapeseed oil, such as Hasten® (Victorian Chemical Company, Australia, hereinbelow referred to as Hasten, main constituent: rapeseed oil ethyl ester), Actirob®B (Novance, France, hereinbelow referred to as ActirobB, main constituent: rapeseed oil methyl ester), Rako-Bino® (Bayer AG, Germany, hereinbelow referred to a Rako-Binol, main constituent: rapeseed oil), Renol® (Stefes, Germany, hereinbelow referred to a Renol, vegetable oil constituent: rapeseed oil methyl ester) or Stefes Mero® (Stefes, Germany, hereinbelow referred to as Mero, main constituent: rapeseed oil methyl ester).

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active ingredients can be applied to the plants, parts of the plants, seeds of the plants or the area under cultivation (soil of a field), preferably to the green plants and parts of the plants and, if appropriate, additionally to the soil of the field. One possible use is the joint application of the active ingredients in the form of tank mixes, the concentrated formulations of the individual active ingredients, in optimal formulations, jointly being mixed with water in the tank and the resulting spray mixture being applied.

A joint herbicidal formulation of the combination according to the invention of the active ingredients (A), (B) and (C) has the advantage of being easier to apply since the quantities of the components are already presented in the correct ratio to each other. Moreover, the adjuvants in the formulation can be matched optimally to each other.

A. General formulation examples a) A dust is obtained by mixing 10 parts by weight of an active ingredient/active ingredient mixture and 90 parts by weight of talc as inert material and comminuting the mixture in a hammer mill.

b) A wettable powder which is readily dispersible in water is obtained by mixing 25 parts by weight of an active ingredient/active ingredient mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active ingredient/active ingredient mixture with 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to 277° C), and grinding the mixture in a ball mill to a fineness of below 5 microns.

d) An emulsifiable concentrate is obtained from 15 parts by weight of an active ingredient/active ingredient mixture, 75 parts by weight of cyclohexanone as solvent and 10 parts by weight of oxethylated nonylphenol as emulsifier.

e) Water-dispersible granules are obtained by mixing 75 parts by weight of an active ingredient/active ingredient mixture, 10 parts by weight of calcium lignosulfonate, 5 parts by weight of sodium lauryl sulfate, 3 parts by weight of polyvinyl alcohol and 7 parts by weight of kaolin, grinding the mixture on a pinned-disk mill and granulating the powder in a fluidized bed by spraying on water as granulation liquid.

f) Water-dispersible granules are also obtained by homogenizing and precomminuting, in a colloid mill, 25 parts by weight of an active ingredient/active ingredient mixture, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

B. Biological Examples

Herbicidal action (field trials)

The seeds or rhizome pieces of typical harmful plants were planted and grown under natural field conditions. Before the harmful plants had emerged or after the harmful plants had emerged, they were treated, as a rule at the 2- to 8-leaf stage, with various dosages of the compositions according to the invention at a water application rate of 100 to 400 I/ha (converted).

After the treatment (approx. 4-6 weeks after application), the herbidical activity of the active ingredients or active ingredient mixtures was scored visually by comparing the treated plots with the untreated control plots. Damage and development of all aerial parts of the plants was recorded. Scoring was done on a percentage scale (100% action=all plants dead; 50% action=50% of the plants and green plant parts dead; 0% action=no discernible action=like control plot). The score figures of in each case 4 plots was averaged.

The results are shown in the tables which follow, the action when using active ingredients (A+B) and (C) independently being stated in brackets.

|  |  | g As/ha | Maize % damage | *Sorghum verticillata* % activity |
|---|---|---|---|---|
| (A + B) C) | (A1 + B2)$^s$ metochlor (C3) + atrazine (C7) | 45 + 1.5 1200 + 625 | 0 0 | 0 75 |
| (A + B) + C) |  | (45 + 1.5) + (1200 + 625) | 0 | 97 (75 + 0) |
| D) (A + B) + D) | nicosulfuron (C15) | 60 (45 + 1.5) + 60 | 0 0 | 74 95 (0 + 74) |

|  |  | g As/ha | Maize % damage | *Polygonum convolvulus* % activity |
|---|---|---|---|---|
| (A + B) E) | (A1 + B2)$^s$ bromoxynil (C33) | 45 + 5 240 | 3 2 | 56 40 |
| (A + B) + E) |  | (45 + 5) + 240 | 15 | 98 (56 + 40) |
| F) (A + B) + F) | dicamba (C20) | 60 (15 + 5) + 60 | 0 0 | 35 95 (56 + 35) |

|  |  | g As/ha | Maize % damage | Setaria spp. % activity |
|---|---|---|---|---|
| (A + B) G) | (A1 + B2)$^s$ halosulfuron (C40) | 45 + 5 36 | 8 3 | 79 0 |
| (A + B) + G) |  | (45 + 5) + 36 | 7 | 87 (79 + 0) |
| H) (A + B) + H) | prosulfuron (C42) | 40 (45 + 5) + 40 | 7 8 | 15 95 (79 + 15) |

Abbreviations:
g AS/ha = application rate in grams of active substance per hectare
(A1 + B2)$^s$ = foramsulfuron + odosulfuron-methyl-sodium + isoxadifen-ethyl (S1-9)

We claim:

1. A herbicide combination with an effective content of components (A), (B) and (C), where (A) denotes one or more herbicides from the group of the compounds of the formula (I) or their salts,

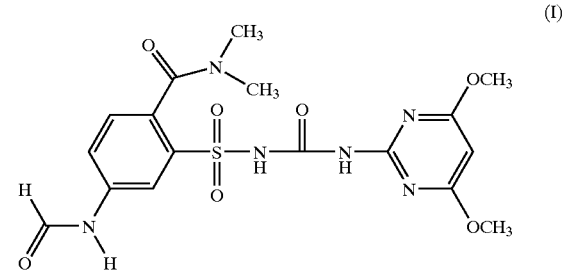

(I)

(B) denotes one or more herbicides from the group of the compounds of the formula (II) and their salts,

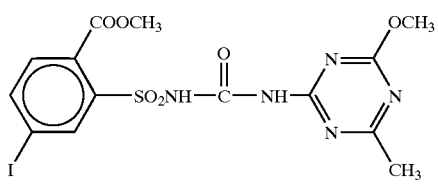 (II)

and (C) denotes one or more herbicides from the group of the compounds consisting of

| (C1) | flumioxazin |
| (C2) | alachlor |
| (C3) | metolachlor |
| (C4) | acetochlor |
| (C5) | dimethenamid |
| (C6) | pethoxamid |
| (C7) | atrazine |
| (C8) | simazine |
| (C9) | cyanazine |
| (C10) | terbuthylazine |
| (C11) | metribuzin |
| (C12) | isoxaflutole |
| (C13) | fluthiamid |
| (C14) | terbutryne |
| (C15) | nicosulfuron |
| (C16) | rimsulfuron |
| (C17) | primsulfuron |
| (C18) | pendimethalin |
| (C19) | sulcotrione |
| (C20) | dicamba |
| (C21) | mesotrione |
| (C22) | linuron |
| (C23) | benoxacor |
| (C24) | metosulam |
| (C25) | flumetsulam |
| (C26) | sethoxydim |
| (C27) | cycloxydim |
| (C28) | clethodim |
| (C29) | clefoxidim |
| (C30) | aclonifen |
| (C31) | MCPA |
| (C32) | 2, 4-D |
| (C33) | bromoxynil |
| (C34) | bentazone |
| (C35) | fluthiacet |
| (C36) | pyridate |
| (C37) | diflufenzopyr |
| (C38) | carfentrazone |
| (C39) | clopyralid |
| (C40) | halosulfuron |
| (C41) | thifensulfuron |
| (C42) | prosulfuron |
| (C43) | tritosulfuron |
| (C44) | sulfosulfuron |
| (C45) | ethoxysulfuron |

-continued

| (C46) | tribenuron |
| (C47) | amidosulfuron |
| (C48) | mecoprop |
| (C49) | dichlorprop |
| (C50) | fluroxypyr |
| (C51) | profluazol |
| (C52) | amicarbazone |
| (C53) | trifloxysulfuron |
| (C54) | glufosinate |
| (C55) | glufosinate-ammonium |
| (C56) | glyphosate |
| (C57) | glyphosate-isopropylammonium |
| (C58) | imazapyr |
| (C59) | imazethapyr |
| (C60) | imazamethabenz |
| (C61) | imazamox |
| (C62) | imazaquin and |
| (C63) | imazapic (AC 263,222). |

2. A herbicide combination as claimed in claim 1, which comprises, as component (A), foramsulfuron, foramsulfuron-sodium or mixtures thereof and, as component (B), iodosulfuron-methyl, iodosulfuron-methyl-sodium or mixtures thereof.

3. A herbicide combination as claimed in claim 1, additionally comprising one or more further components from the group consisting of agrochemically active ingredients of a different type, formulation auxiliaries and additives conventionally used in crop protection.

4. A herbicide combination as claimed in claim 1, additionally comprising one or more safeners.

5. A herbicide combination as claimed in claim 1, which additionally comprises one or more fatty alcohol polyglycol esters, one or more vegetable oils or mixtures thereof.

6. A method for controlling undesired vegetation, which comprises applying, jointly or separately, the herbicides (A), (B) and (C) as defined in claim 1 to the plants, plant parts, the seeds of the plants or the area on which the plants grow.

7. The method as claimed in claim 6 for the selective control of harmful plants in plant crops.

8. The method as claimed in claim 7 for the control of harmful plants in corn.

9. The method as claimed in claim 7, wherein the plant crops are genetically modified or obtained by mutation/selection.

10. A method of using the herbicide combination of claim 1, comprising the step of applying the combination to a locus for controlling harmful plants.

* * * * *

UNITED STATES PATENT AND TRADEMARK OFFICE
CERTIFICATE OF CORRECTION

PATENT NO. : 6,750,177 B2
DATED : June 15, 2004
INVENTOR(S) : Erwin Hacker et al.

It is certified that error appears in the above-identified patent and that said Letters Patent is hereby corrected as shown below:

Title page,
Item [56], References Cited, U.S. PATENT DOCUMENTS, reads "5,648,315 A" should read -- 5,648,315 B1 --, "5,925,597 A" should read -- 5,925,597 B1 --.

Signed and Sealed this

Twenty-second Day of February, 2005

JON W. DUDAS
*Director of the United States Patent and Trademark Office*